(12) United States Patent
Zollinger et al.

(10) Patent No.: US 6,543,236 B2
(45) Date of Patent: Apr. 8, 2003

(54) HYPERPOLARIZED NOBLE GAS EXTRACTION METHODS, MASKING METHODS, AND ASSOCIATED TRANSPORT CONTAINERS

(75) Inventors: David L. Zollinger, Chapel Hill, NC (US); Kenton C. Hasson, Durham, NC (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 10/160,944

(22) Filed: May 31, 2002

(65) Prior Publication Data

US 2002/0152756 A1 Oct. 24, 2002

Related U.S. Application Data

(62) Division of application No. 09/828,636, filed on Apr. 6, 2001, now Pat. No. 6,427,452, which is a division of application No. 09/568,859, filed on May 9, 2000, which is a division of application No. 09/163,721, filed on Sep. 30, 1998, now Pat. No. 6,237,363.

(51) Int. Cl.[7] .............................. B67D 5/00; B67D 5/42; G01F 11/00
(52) U.S. Cl. ............................ 62/3.1; 222/3; 222/386.5
(58) Field of Search ...................... 62/51.1, 3.1; 222/3, 222/386.5, 389

(56) References Cited

U.S. PATENT DOCUMENTS 2,865,541 A * 12/1958 Hicks ...................... 222/386.5

(List continued on next page.)

FOREIGN PATENT DOCUMENTS

EP 0933062 A2 4/1999

(List continued on next page.)

OTHER PUBLICATIONS

Albert et al., $^{129}$Xe Relaxation Catalysis by Oxygen, Abstracts of the 11th Annual Meetings of the Society for Magnetic Resonance Medicine, (1992).

(List continued on next page.)

Primary Examiner—William C. Doerrler
(74) Attorney, Agent, or Firm—Myers Bigel Sibley & Sajovec PA

(57) ABSTRACT

Methods of extracting and removing hyperpolarized gas from a container include introducing an extraction fluid into the container to force the hyperpolarized gas out of an exit port. The hyperpolarized gas is forced out of the container separate and apart from the extraction fluid. Alternatively, if the fluid is a gas, a portion of the gas is mixed with the hyperpolarized gas to form a sterile mixed fluid product suitable for introduction to a patient. An additional method includes engaging a gas transfer source such as a syringe to a transport container and pulling a quantity of the hyperpolarized gas out of the container in a controlled manner. Another method includes introducing a quantity of liquid into a container and covering at least one predetermined internal surface or component with the liquid to mask the surfaces and keep the hyperpolarized gas away from the predetermined internal surface, thereby inhibiting any depolarizing affect from same. Examples of surfaces or components suitable for masking include valves, seals, and the like. Yet another extraction method includes expanding a resilient member inside the container to force the hyperpolarized gas to exit therefrom. Containers include a resilient member positioned in fluid communication with the hyperpolarized gas in the container. An additional container includes inlet and outlet ports in fluid communication with the chamber and positioned on opposing sides or end portions of the container. Another container includes a port configured to receive a portion of a syringe therein. An additional aspect of the disclosure relates to calibration methods and apparatus for identifying the hyperpolarization status of the gas.

20 Claims, 16 Drawing Sheets

U.S. PATENT DOCUMENTS

| | | | | |
|---|---|---|---|---|
| 3,508,686 A | * | 4/1970 | Goldberg | 222/135 |
| 3,552,394 A | | 1/1971 | Horn | 128/218 |
| 3,657,363 A | | 4/1972 | Dorko | 260/642 |
| 3,748,864 A | | 7/1973 | Lofredo et al. | 62/22 |
| 3,858,572 A | | 1/1975 | Binard et al. | 128/2 A |
| 3,893,278 A | | 7/1975 | Lewis | 53/5 |
| 3,926,176 A | | 12/1975 | Winchell et al. | 250/506.1 |
| 3,945,539 A | | 3/1976 | Sossong | 222/386.5 |
| 3,966,781 A | | 6/1976 | Atkinson et al. | 260/410.9 R |
| 4,080,429 A | | 3/1978 | Koeppe et al. | 423/262 |
| 4,367,737 A | | 1/1983 | Kozam et al. | 128/215 |
| 4,369,048 A | | 1/1983 | Pence | 55/66 |
| 4,417,909 A | | 11/1983 | Weltmer, Jr. | 62/12 |
| 4,450,407 A | | 5/1984 | Kwon et al. | 324/304 |
| 4,586,511 A | | 5/1986 | Clark, Jr. | 128/653 |
| 4,599,462 A | | 7/1986 | Michl | 568/702 |
| 4,755,201 A | | 7/1988 | Eschwey et al. | 62/12 |
| 4,775,522 A | | 10/1988 | Clark, Jr. | 424/9 |
| 4,914,160 A | | 4/1990 | Azizian | 525/329.3 |
| 4,977,749 A | | 12/1990 | Sercel | 62/51.1 |
| 5,007,243 A | | 4/1991 | Yamaguchi et al. | 62/51.1 |
| 5,039,500 A | | 8/1991 | Shino et al. | 423/262 |
| 5,161,382 A | | 11/1992 | Missimer | 62/46.1 |
| 5,545,396 A | | 8/1996 | Albert et al. | 424/93 |
| 5,551,601 A | * | 9/1996 | Camm et al. | 222/105 |
| 5,612,103 A | | 3/1997 | Driehuys et al. | 428/34.7 |
| 5,617,860 A | | 4/1997 | Chupp et al. | 128/653.4 |
| 5,642,625 A | | 7/1997 | Cates, Jr. et al. | 62/55.5 |
| 5,785,953 A | | 7/1998 | Albert et al. | 424/93 |
| 5,809,801 A | | 9/1998 | Cates, Jr. et al. | 62/637 |
| 5,860,295 A | | 1/1999 | Cates, Jr. et al. | 62/637 |
| 5,934,103 A | | 8/1999 | Ryan et al. | 62/637 |
| 5,936,404 A | | 8/1999 | Ladebeck et al. | 324/300 |
| 6,085,743 A | | 7/2000 | Rosen et al. | 128/200.24 |
| 6,168,048 B1 | * | 1/2001 | Xu et al. | 222/1 |

FOREIGN PATENT DOCUMENTS

| | | |
|---|---|---|
| FR | 2226145 | 11/1974 |
| FR | 2744932 | 8/1997 |
| GB | 194704 | 8/1823 |
| WO | PCT/US97/05004 | 3/1997 |
| WO | PCT/US97/05084 | 3/1997 |
| WO | PCT/US97/05166 | 3/1997 |
| WO | WO 97/29836 | 8/1997 |
| WO | WO 97/37177 | 10/1997 |
| WO | WO 97/37178 | 10/1997 |
| WO | WO 97/37239 | 10/1997 |
| WO | WO 98/58272 | 12/1998 |
| WO | WO 99/07415 | 2/1999 |
| WO | WO 99/14582 | 3/1999 |
| WO | WO 99/25243 | 5/1999 |
| WO | WO 99/17105 | 8/1999 |
| WO | WO 99/17304 | 8/1999 |
| WO | WO 99/66254 | 12/1999 |
| WO | WO 99/66255 A2 | 12/1999 |
| WO | WO 99/66255 A3 | 12/1999 |
| WO | WO 00/21601 | 4/2000 |

OTHER PUBLICATIONS

Albert et al., *Relaxation of $^{129}Xe$ in Model Biological Systems: On Probing the Mechanism of General Anesthesia*, Abstracts of the 11th Annual Meetings of the Society for Magnetic Resonance Medicine, (1992).

Arimoto, et al., "Development of Measurement and Control System for Polarized $^3He$ Ion Source Based on Electron Pumping," The 11th Symposium on Accelerator Science and Technology, Harima Science Garden City, pp. 14–16 (1997).

Augustine et al., *Low field magnetic resonance images of polarized noble gases obtained with a dc superconducting quantum interference device*; App. Phy. Ltrs., vol. 72, No. 15, pp. 1908–1910 (Apr. 13, 1998).

Becker et al., *Study Of Mechanical Compression Of Spin–Polarized $^3He$ Gas*, Nuclear Instruments And Methods In Physics Research, vol. A 346, pp. 45–51 (1994).

Bhaskar et al., *Efficiency of Spin Exchange between Rubidium Spins and $^{129}Xe$ Nuclei in a Gas*, Physical Review Letters, vol. 49, No. 1, pp. 25–28 (Jul. 5, 1982).

Bouchiat et al., "Relaxation of Optically Pumped Rb Atoms on Paraffin–Coated Walls," Phys. Rev., vol. 147, No. 1 (Jul. 8, 1966).

Brochure, Jensen Inert Products, *Gas Sampling Bags*, jensen@jenseninert.com (Copyright 1997).

Brunner et al., "Communications: Gas Flow MRI Using Circulating Laser–Polarized $^{129}Xe$," J. Mag. Res. vol. 138, pp. 155–159 (1999).

Cain et al., Nuclear Spin Relation Mechanisms and Mobility of Gases in Polymers, 94 J. Phys. Chem. No. 5, pp. 2128–2135 (1990).

Cates et al., *Laser Production of Large Nuclear–Spin Polarization in Frozen Xenon*, Phys. Rev. Lett., vol. 65, No. 20, pp. 2591–2594 (Nov. 12, 1990).

Cates et al., *Rb–$^{129}Xe$ spin–exchange rates due to binary and three–body collisions at High Xe pressures*, Physical Review A, vol. 45, pp. 4631–4639 (Apr. 1, 1992).

Cummings et al., *Optical pumping of Rb vapor using high–power $Ga_{1-x}A_x$ As diode laser arrays*, Phys. Rev. A, vol. 51, No. 6, pp. 4842–4851 (Jun. 1995).

Driehuys et al., *High–volume production of laser–polarized $^{129}Xe$*, 69 App. Phys. Lett. (12), pp. 1668–1670 (Sep. 16, 1996).

Driehuys et al., *Surface Relaxation Mechanisms of Laser–Polarized $^{129}Xe$*, 74 Phys. Rev. Lett., No. 24, pp. 4943–4946 (Jun. 12, 1995).

Freed, *Dynamic effects of pair correlation functions on spin relaxation by translational diffusion in liquid II. Finite jumps and independent $T_1$ processes*, 68 J. Chem. Phys., vol. 9, pp. 4034–4037 (May 1, 1978).

Gao et al., *Magnetization and Diffusion Effects in NMR Imaging of Hyperpolarized Substances*, Magn. Reson. Med., vol. 37, No. 1, pp. 153–158 (Jan. 1997).

Gatzke et al., *Extraordinarily Slow Nuclear Spin Relaxation in Frozen Lazer–Polarized $^{129}$ Xe*, Phys. Rev. Lett., vol. 70, No. 5, pp. 690–693 (Feb. 1, 1993).

Haeberli, "Storage Cell Target for Polarized Proton and Antiproton Rings," Int'l . Workshop on Polarized Ioin Sources and Polarized Gas Jets, Y. Mori Editor, pp. 35–44 (1990).

Happer et al., *An Optical Pumping Primer*, Hyperfine Interactions, vol. 38, pp. 435–470 (1987).

Heil et al., *Very long nuclear relaxation times of spin polarized helium 3 in metal coated cells*, Physics Letters A, vol. 201, pp. 337–343 (May 29, 1995).

Hunt et al., *Nuclear Magnetic Resonance of $^{129}Xe$ in Natural Xenon*, 130 Phys. Rev., No. 6, pp. 2302–2305 (Jun. 15, 1963).

Hwang et al., *Dynamic effects of pair correlation functions on spin relaxation by translational diffusion in liquids*, 63 J. Chem. Phys., No. 9, pp. 4017–4025 (1975).

Kaatz et al., *A comparison of molecular hyperpolarizabilities from gas and liquid phase measurements*; J. Chem. Phys., vol. 108, No. 3, pp. 849–856 (Jan. 15, 1998).

Kauczor et al., *MRI using hyperpolarized noble gases*, Abstract, Eur. Radiol., vol. 8, No. 5 (1998).

Kauczor et al., *The helium–3 MRT of pulmonary ventilation; the initial clinical applications*, Abstract, Rofo Fortschr Geb Rontgenstru Neuen Bildegeb Verfahr, vol. 166, No. 3 (Mar. 1997).

Laloe et al., Workshop on Polarized $^3$He Beams and Targets, AIP ConfProx #131 (1984).

Middleton et al., *MR Imaging With Hyperpolarized $^3$He Gas*, Magnetic Resonance In Medicine, vol. 33, pp. 271–275 (1995).

Middleton, The Spin Structure of the Neutron Determined Using A Polarized $^3$He Target, Ph.D. Dissertation, Princeton University (1994).

Miller et al., Xenon NMR: Chemical shifts of a general anesthetic common solvents, proteins, and membranes, Proc. of the Nat. Academy of Science (USA), vol. 78, No. 8, pp. 4946–4949 (Aug. 1981).

Mugler et al., *MR Imaging and Spectroscopy Using Hyperpolarized $^{129}$Xe Gas: Preliminary Human Results*, Magn. Reson. Med., vol. 37, No. 6, pp. 809–815 (Jun. 1997).

Nacher et al., *Recent results on hyperpolarized $^3$He–$^4$He liquid mixtures*, vol. 46, Supp. Pt. S6, pp. 3025–3032 (Aug. 1966).

Newbury et al., *Gaseous $^3$He–$^3$He Magnetic Dipolar Spin Relaxation*, 48 Phys. Rev. A., No. 6, p. 4411–4420 (Dec. 1993).

Patyal et al., *Longitudinal Relaxation and Diffusion Measurements Using Magnetic Resonance Signals from Laser–Hyperpolarized $^{129}$Xe Nuclei*, J. Magn. Reson., vol. 126, pp. 58–65 (May 1997).

Pauly, *Permeability and Diffusion Data*, The Polymer Handbook, VI/435–449.

PCT International Search Report mailed May 31, 2000, PCT International Application No. PCT/US99/22990.

Raftery et al., *NMR of optically pumped xenon thin films*, Chem. Phys. Lett., vol. 191, pp. 385–390 (Apr. 10, 1992).

Reif, *Fundamentals of Statistical and Thermal Physics*, McGraw–Hill, Ch. 12–14, pp. 461–493 (1965).

Romalis et al., "Accurate $^3$He Polarimetry Using the Rb Zeeman Frequency Shift Due to the Rb–$^3$He Spin–Exchange Collisions," Phys. Rev. A, vol. 58, No. 4, pp. 3004–3011 (Oct. 1998).

Ruth et al., "Production of Nitrogen–Free, Hyperpolarized $^{129}$Xe Gas," Appl. Phys. B, vol. 68, pp. 93–97 (1991).

Saam et al., "Low Frequency NMR Polarimeter for Hyperpolarized Gases," Journal of Magnetic Resonance, vol. 134, pp. 67–71 (1998).

Saam et al., Edge Enhancement Observed with Hyperpolarized $^3$ HE, Chem. Phys. Ltrs., vol. 263, pp. 481–487 (1996).

Saam et al., *Nuclear relaxation of$^3$ He in the presence of $O_2$*, Phys. Rev. A, vol. 52, pp. 862–865 (Jul. 1995).

Sauer et al., Laser Polarized Liquid Xenon, Chem. Phys. Lett., vol. 277, pp. 153–158 (Oct. 3, 1997).

Schearer, *Optical Pumping of Neon$^3$P2 Metastable Atoms*, Phys Rev., vol. 180, No. 1, pp. 83–90 (Apr. 5, 1969).

Song et al., *Effects of diffusion on magnetic resonance imaging of laser–polarized xenon gas*, J. Chem. Phys., vol. 108, No. 15, pp. 6233–6239 (Apr. 15, 1998).

Surkau et al., "Large Hyperpolarized $^3$He quantities for $^3$He–MRI of the Lung," Proceedings of the Int'l. Soc. For Mag. Reson. In Med., Fifth Scientific Meeting and Exhibition, Vancouver, BC, Canada, 1, 182 XP002116424 (Apr. 12–18, 1997).

Wagshul et al., "Laser Optical Pumping of High–Density Rb in Polarized $^3$He Targets," Phys. Rev. A, vol. 49, p. 3854–3869 (1994).

Wagshul et al., "Optical Pumping of High–Density Rb With a Broadband Dye Laser and GaAlAs Siode Laser Arrays: Application to $^3$He Polarization," Phys. Rev. A., vol. 40, No. 8, pp. 4447–4454 (1989).

Wagshul et al., *In Vivo MR Imaging and Spectroscopy Using Hyperpolarized $^{129}$Xe*, Magn. Reson. Med., vol. 36, No. 2, pp. 183–191 (1996).

Wu et al., "Experimental Studies of Wall Interactions of Adsorbed Spin–Polarized $^{131}$Xe Nuclei," Phys. Rev. A, vol. 42, No. 5 (Sep. 01, 1990).

Yonehara et al., "Design of Rb Cell for Polarized $^3$He Ion Source Based on Electron Pumping," The 11th Symp. on Accelerator Sci. & Tech., Harima Sci. Garden City, pp. 174–175 (1997).

Zeng et al., *Experimental determination of the rate constants for spin exchange between optically pumped K, Rb, and Cs Atoms and $^{129}$Xe nuclei in alkali–metal—noble–gas van der Waals molecules*, Physical Review A, vol. 31, pp. 260–278 (Jan. 1985).

Zeng et al., "Wall Relaxation of Spin Polarized $^{129}$Xe Nuclei," Phys. Ltrs., vol. 96A, No. 4 (Jun. 27, 1983).

PCT International Search Report, International Application No. PCT/US01/08237 mailed Sep. 3, 2002.

\* cited by examiner

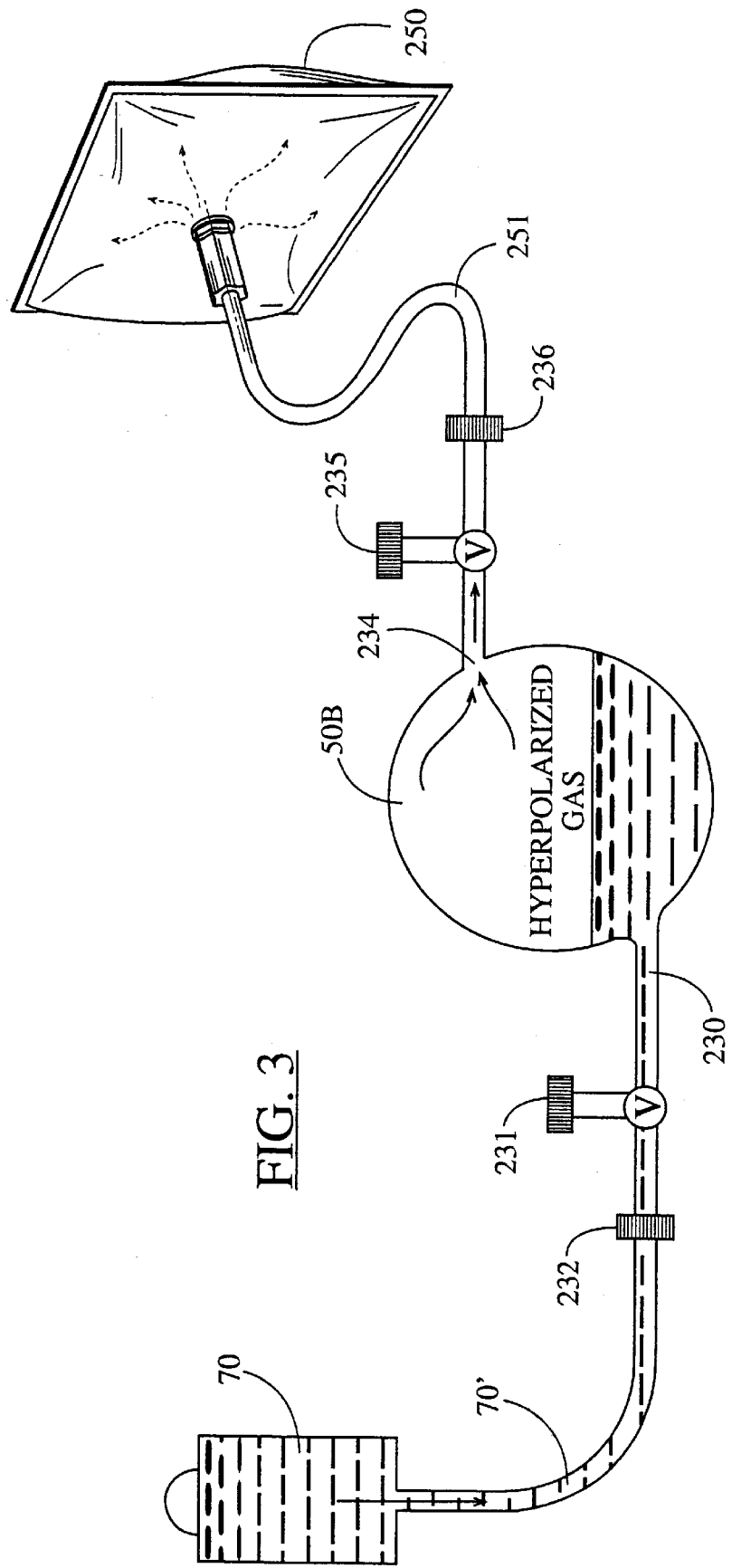

HYPERPOLARIZED NOBLE GAS EXTRACTION METHODS, MASKING METHODS, AND ASSOCIATED TRANSPORT CONTAINERS

RELATED APPLICATIONS

This application is a divisional application of U.S. patent application Ser. No. 09/828,636, filed Apr. 6, 2001, now U.S. Pat. No. 6,427,452 and Ser. No. 09/568,859 filed May 9, 2000, which are divisionals of U.S. patent application Ser. No. 09/163,721, filed Sep. 30, 1998, now the U.S. Pat. No. 6,237,363, the contents of which are hereby incorporated by reference as if recited in full herein.

GOVERNMENT GRANT INFORMATION

This invention was made with Government support under Grant No. NIH 7R44HL59022-03. The U.S. Government has certain rights in this invention.

FIELD OF THE INVENTION

The present invention relates to equipment and methods used to remove or dispense hyperpolarized gases from containers. The invention is particularly suitable for dispensing sterile or pharmaceutical hyperpolarized gases for Magnetic Resonance Imaging ("MRI") applications.

BACKGROUND OF THE INVENTION

Conventionally, MRI has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium-3 ("$^3$He") and Xenon-129 ("$^{129}$Xe") have been found to be particularly suited for this purpose. Unfortunately, as will be discussed further below, the polarized state of the gases is sensitive to handling and environmental conditions and can potentially rapidly decay from the polarized state.

Hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. No. 5,545,396 to Albert et al., the disclosure of which is hereby incorporated by reference as if recited in full herein.

The hyperpolarized gas is typically produced by spin-exchange with an optically pumped alkali metal. The alkali metal is removed from the hyperpolarized gas prior to introduction into a patient to form a non-toxic and/or sterile composition. Unfortunately, the hyperpolarized state of the gas can deteriorate or decay relatively quickly and therefore must be handled, collected, transported, and stored carefully.

The "$T_1$" decay constant associated with the hyperpolarized gas' longitudinal relaxation time is often used to describe the length of time it takes a gas sample to depolarize in a given situation. The handling of the hyperpolarized gas is critical because of the sensitivity of the hyperpolarized state to environmental and handling factors and the potential for undesirable decay of the gas from its hyperpolarized state prior to the planned end use, i.e., delivery to a patient for imaging. Processing, transporting, and storing the hyperpolarized gases—as well as delivery of the gas to the patient or end user—can expose the hyperpolarized gases to various relaxation mechanisms such as magnetic gradients, contact-induced relaxation, paramagnetic impurities, and the like.

In the past, rigid containers have been used to transport the hyperpolarized gas from a polarization site to an imaging site such as a hospital. Unfortunately, these conventional transport containers can leave relatively large residual amounts of the gas in the container at the end use point. For example, absent active pumping (which generally introduces unacceptable depolarization to the hyperpolarized gas) an atmosphere of hyperpolarized gas typically remains in the transport vessel, in equilibrium with the ambient air pressure. As such, a larger volume of gas is typically transported to the imaging site to provide the volume desired for clinical use. Unfortunately, the hyperpolarized gas is relatively expensive to produce and this wasted residual gas can disadvantageously escalate the cost of the hyperpolarized product even further. Further, as noted above, conventional pump delivery systems which attempt to extract the gas from the transport container can cause the polarization of the hyperpolarized gas to rapidly decay, thereby limiting the life of the product and providing potentially severe time constraints in which successful clinical imaging can be performed.

Accordingly, there is a need to provide improved extraction systems and containers to minimize the depolarizing effect of the extraction system and to efficiently deliver the hyperpolarized gas to the desired subject.

OBJECTS AND SUMMARY OF THE INVENTION

In view of the foregoing, it is an object of the present invention to provide improved methods to extract hyperpolarized gases from collection and transport vessels in a way which minimizes the de-polarization of the gas attributed thereto.

It is another object of the invention to reduce the residual amounts of hyperpolarized gas in collection vessels or transport vessels at the end use site.

It is yet another object of the invention to provide improved gas dispensing methods and associated containers and apparatus to minimize any degrading effect that the dispensing may have on the polarized life of a hyperpolarized product so that the hyperpolarized product retains sufficient polarization at the end use site to allow effective imaging at delivery.

It is still another object of the present invention to provide dual purpose transport containers which are configured to both collect and transport the hyperpolarized gas.

It is another object of the present invention to provide improved containers which are configured to minimize depolarizing activity associated with the dispensing and delivery of the hyperpolarized gas to a subject.

It is yet another object of the invention to provide methods and apparatus which can minimize the de-polarizing effects on the hyperpolarized state of the gas attributed to active dispensing of the gas from a polarization cell, collection, or transport vessel.

It is an additional object of the present invention to provide a masking method which inhibits the direct contact of hyperpolarized gas with a potentially de-polarizing material or surface.

It is another object of the present invention to provide a polarization verification method which can identify the expiration date of the hyperpolarized gas externally so that hospital personnel can visually determine the status of the gas prior to delivery to a patient.

These and other objects are satisfied by the present invention which is directed to hyperpolarized gas extraction systems, methods, and associated containers which are configured to remove or extract the hyperpolarized gas from a container and reduce the amount of residual gases unrecovered therefrom in a way which minimizes the depolarization of the hyperpolarized gas. In particular, a first aspect of the present invention is directed to a method for extracting a quantity of hyperpolarized noble gas from a container which includes directing a liquid into a container holding a quantity of hyperpolarized gas therein. The liquid contacts the hyperpolarized gas and forces the gas to exit the container separate from the liquid into an exit path operably associated with the container, thereby extracting the hyperpolarized noble gas from the container. In a preferred embodiment, the liquid comprises water which has been sterilized and partially, and more preferably, substantially de-oxygenated and/or de-ionized.

Another aspect of the present invention is directed towards a method similar to that described above, but this method introduces a quantity of fluid (such as gas or liquid) into the container to push the hyperpolarized gas out of the container. The liquid aspect is similar to that described above.

In one embodiment, wherein the fluid is a gas, the gas is preferably non-toxic and suitable for inhalation by a patient. As such, the extraction gas can mix with the hyperpolarized gas to form a hyperpolarized gas mixture as it exits from the container.

In another embodiment, the hyperpolarized noble gas exits the container separate from the extraction gas. In this embodiment, the extraction gas has a density which is substantially different from the hyperpolarized gas. For example, for $^{129}$Xe, the extraction gas is preferably selected so that the hyperpolarized gas has a density which is greater than the extraction gas so that the extraction gas has a density which is less than the hyperpolarized gas. In this embodiment, the exit path is preferably positioned on the bottom portion of the container during the extraction while the extraction gas is introduced into the top portion of the container. This allows the heavier $^{129}$Xe to exit out of the bottom of the container while the lighter weight extraction gas remains therein.

In another embodiment, the hyperpolarized gas is $^3$He, and the extraction gas is preferably selected such that it has a density which is greater than that of $^3$He. In this embodiment, the exit path is preferably positioned on the top portion of the container while the extraction gas is introduced into the bottom of the container. As such, the lighter $^3$He exits from the top of the container while the heavier extraction gas remains in the container.

In an additional aspect of the present invention, the extraction method includes engaging a gas transfer source with the container and drawing a quantity of hyperpolarized gas from a container such that the gas is controllably removed therefrom. In a preferred embodiment, the gas transfer source is a syringe which is inserted into the sealed exit path (via an access port) of the container to remove the hyperpolarized gas therefrom. Preferably, the gas transfer source is configured with gas contact surfaces which are friendly to the hyperpolarized state of the gas, i.e., coated with or formed of materials which do not cause excessive depolarization or which inhibit depolarization.

Another aspect of the present invention is directed to a method of masking the potentially depolarizing effects of internal components or surface areas associated with the container. This method includes introducing a quantity of fluid (preferably a liquid) into the container and covering at least one predetermined exposed internal surface of the container with the fluid (liquid) to inhibit direct contact between the internal surface and the hyperpolarized noble gas, thereby masking the exposed surface with a fluid (liquid) to inhibit the depolarization of the gas in the container. In a preferred embodiment, the container is oriented to direct the masking fluid (liquid) into the desired area and the predetermined area includes covering a valve or seal in fluid communication with the container.

Yet another aspect of the invention is directed to a method of decreasing the residual amount of hyperpolarized gas remaining in the container when not using an active pumping or removal system. The method includes introducing a quantity of hyperpolarized noble gas into a small container (preferably less than about 500 cm$^3$, and more preferably less than about 200 cm$^3$) at a pressure of about 3–10 atm. The container is then sealed and transported to a use site remote from the polarization site where the container is opened to release the gas by allowing the container to depressurize to ambient pressure. This is a high pressure, low volume container/method which decreases the amount of residual gas left in low pressure, relatively high volume containers typical of conventional delivery methods/containers. This method is particularly suitable for $^3$He as higher pressures introduced to the hyperpolarized $^3$He still yield relatively long $T_1$'s.

An additional aspect of the invention is directed to a method of extracting hyperpolarized gas from a container by positioning a resilient member in fluid communication with the internal chamber of the container holding hyperpolarized noble gas. The resilient member is then expanded to extend into the container and contact the hyperpolarized gas. The gas is forced to exit the container away from the expanded resilient member. Preferably, the resilient member is sealed to the container to prevent the fluid used to expand or inflate the resilient member from contacting the hyperpolarized noble gas. Also, it is preferred that the resilient member be formed from or coated with a material which is friendly to polarization of the gas in the container. Stated differently, a material which is (substantially) not depolarizing to or which inhibits depolarization associated with surface contact with the hyperpolarized gas.

Another aspect of the present invention is directed to improved containers for processing and transporting hyperpolarized gases. In one embodiment, the container comprises a chamber and a quantity of hyperpolarized gas disposed therein. The container includes a resilient member which is positioned to be in communication with the hyperpolarized gas in the chamber. The resilient member has a first collapsed position and a second expanded position. When in the second position, the resilient member extends into the chamber a further distance relative to the first position. Preferably, the resilient member expands and retracts responsive to fluid introduced into an inlet port operably associated with the resilient member. Also, it is preferred that the resilient member is sealed such that it inhibits any expansion fluid from contacting the hyperpolarized gas. In operation, the expansion of the resilient member pushes/forces the hyperpolarized gas to exit the container, thereby actively forcing the hyperpolarized gas out of the container. Advantageously, this configuration can minimize the residual amounts of the gas left in the container while also minimizing potentially depolarizing interactions attributed to the active removal apparatus.

In an alternative embodiment, the container includes a hyperpolarized gas holding chamber and a quantity of hyperpolarized gas disposed therein. The container also includes an access port which is in fluid communication with the holding chamber and which is resiliently configured to receive a portion of a syringe therein. Preferably, the container also includes a valve and an externally accessible connector, such as a lure or septum type connection, which provides an "air-tight" seal for drawing the hyperpolarized gas from the container in a manner which minimizes the possibility of the introduction of air therewith. Preferably, the syringe plunger and body and septum are formed from or coated with polarization friendly materials. Advantageously, controlled amounts of the gas can be removed from the transport vessel and conveniently be delivered to the patient by simply reversing the plunger to inject or deliver the desired quantity of hyperpolarized gas without complex machinery and the like. Additionally, masking liquid can be used in the container as noted above.

In an additional embodiment, the container comprises a gas holding chamber, a quantity of hyperpolarized gas, and two ports (an inlet port and an outlet port) in fluid communication with the chamber. The inlet and outlet ports are positioned on different sides of the chamber. Preferably, the two ports are radially misaligned and positioned at least 90 degrees apart from the other. It is also preferred that the two ports be offset relative to the other. For example, in one embodiment (during extraction of the gas) the exit port is above the inlet port. Similarly, in another embodiment, the inlet port is above the exit port.

The containers or transport vessels are preferably configured to reduce surface or contact depolarization by forming a contact surface of a material of a thickness which acts to minimize any associated surface or contact depolarization. In addition, the outer layer is preferably configured to define an oxygen shield overlying the inner layer and is configured to minimize the migration of oxygen into the container. Suitable materials and thicknesses and the like are described in co-pending application to Deaton et al., U.S. patent application Ser. No. 09/126,448, filed Jul. 30, 1998, entitled Containers for Hyperpolarized Gases and Associated Methods, and identified by Attorney Docket number 5770-12. The contents of this disclosure is hereby incorporated by reference as if recited in full herein. More preferably, the container material comprises one or more of a high-purity metal film, high-purity impermeable glass, high-purity metal oxide, and high-purity insulator or semiconductor (for example, high purity silicon).

It is additionally preferred that the container use seals such as O-rings which are substantially free of paramagnetic impurities. The proximate position of the seal with the hyperpolarized gas can make this component a dominant factor in the depolarization of the gas. Accordingly, it is preferred that the seal or O-ring be formed from substantially pure polyethylene or polyolefins such as ethylene, propylene, copolymers and blends thereof. Of course, fillers which are friendly to the hyperpolarization can be used (such as substantially pure carbon black and the like). Alternatively, the O-ring or seal can be coated with a surface material such as LDPE or deuterated HDPE or other low-relaxivity property material or high purity metal.

Another aspect of the present invention is directed towards a method for improving the transfer efficiency of the hyperpolarized gas such as from the polarization cell in the hyperpolarization apparatus. Preferably, the method comprises the steps of positioning a chamber in fluid communication with the polarization cell, directing a quantity of hyperpolarized gas out of the polarization cell and into the chamber, and cooling the chamber to improve the transfer of hyperpolarized gas from the polarization cell. Preferably, the cooling step cools the container substantially, such as below the freezing point of water, and more preferably to the temperature of dry ice (195 K), and most preferably to cryogenic temperatures (such as by exposing the chamber to a bath of liquid nitrogen (77 K)). In one embodiment, the hyperpolarized gas is $^3$He. In another embodiment, the chamber is closed or configured to capture all the gas exiting the polarization cell. Advantageously, the cooling of the chamber can increase the pressures and volumes of gas received into the chamber (and thus out of the polarization cell), improving the transfer efficiency thereby.

Still another aspect of the present invention is a method of identifying the hyperpolarization state of a quantity of hyperpolarized gas (preferably at a use-facility or site). The method includes positioning a container having a quantity of hyperpolarized substance in a magnetic field and determining the polarization level of the hyperpolarized substance in the container. An externally visible indicia of polarization, i.e., an identifying mark such as a use-by date is affixed to the container. The identified container is then protected from de-polarizing factors. For example, storing the identified container in a stable magnetic field. Advantageously, this identification can preclude or minimize the delivery of inactive gases to a patient by indicating a shelf life associated with a desired level of polarization of the hyperpolarized substance in the container to hospital personnel. Preferably, the magnetic field has a low field strength, and the determining step includes transmitting a signal to the hyperpolarized substance in the container and receiving a signal back therefrom. The signal back corresponds to the hyperpolarization level of the substance in the container.

Advantageously, the methods and containers of the present invention can improve the relaxation time (i.e., lengthen the $T_1$) of the hyperpolarized gas such as by allowing active dispensing of the gas from a container in a manner which inhibits depolarization of the hyperpolarized gas. Further, the active dispensing can reduce the amount of residual gases left in the container at the removal point, thereby improving the delivery efficiency.

The foregoing and other objects and aspects of the present invention are explained in detail herein.

BRIEF DESCRIPTION OF THE DRAWINGS

FIG. 3 is a schematic illustration of another embodiment of a liquid extraction system showing an alternate container and a patient delivery bag according to the present invention.

DETAILED DESCRIPTION OF THE PREFERRED EMBODIMENTS

Figure 1:
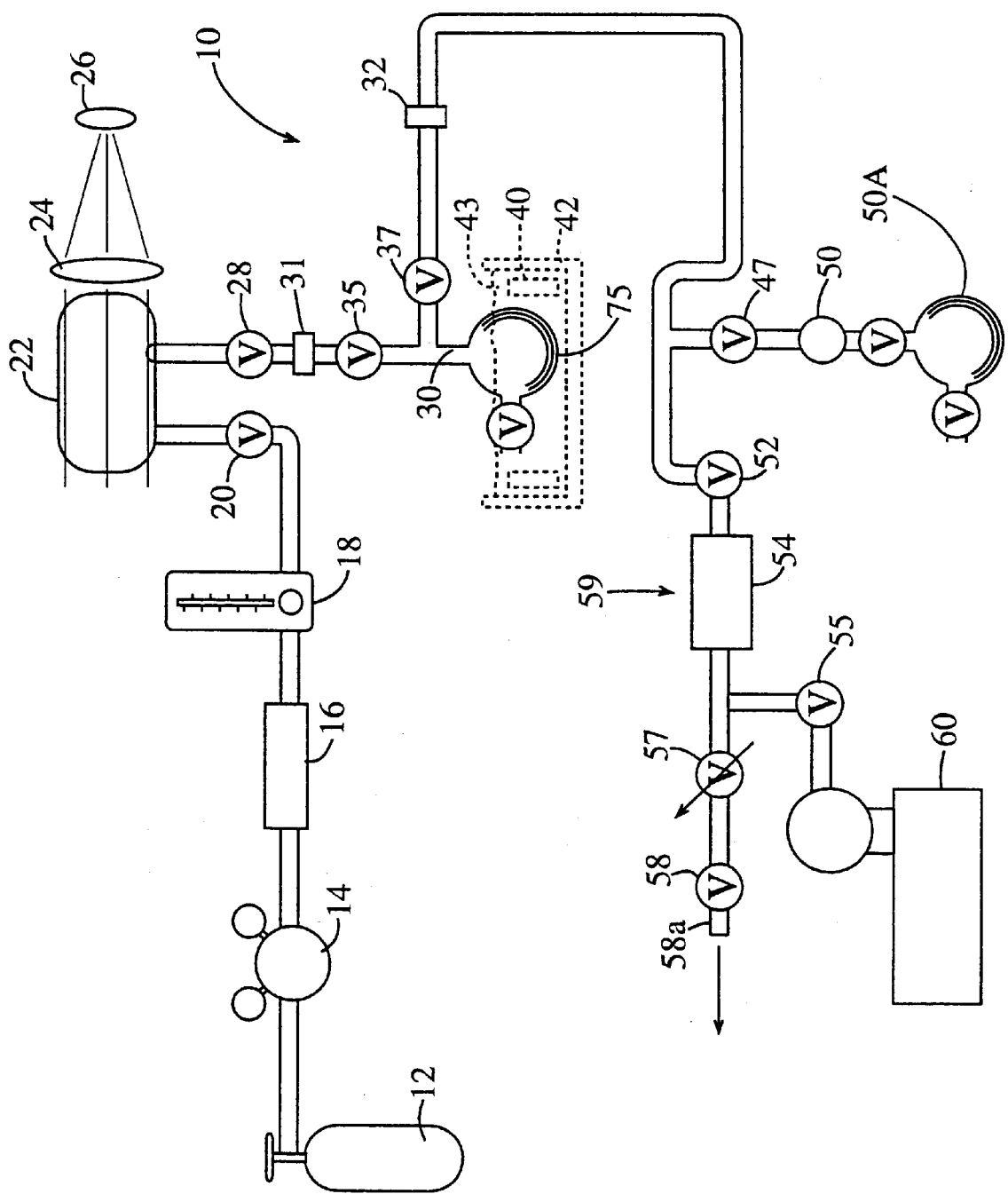
FIG. 1 is a schematic illustration of a xenon hyperpolarizer apparatus showing a container according to one embodiment of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity. For ease of discussion, the term "hyperpolarized gas" will be used to describe a hyperpolarized gas alone, or a hyperpolarized gas which contacts or combines with one or more other components, whether gaseous, liquid, or solid. Thus, the hyperpolarized gas described herein can be a hyperpolarized gas composition/mixture (preferably non-toxic such that it is suitable for in vivo introduction) such that the hyperpolarized noble gas can be combined with other noble gases and/or other inert or active components. Also, as used herein, the term "hyperpolarized gas" can include a product in which the hyperpolarized gas is dissolved into another liquid (such as a carrier fluid) or processed such that it transforms into a substantially liquid state, i.e., "a liquid polarized gas". Thus, although the term includes the word "gas", this word is used to name and descriptively track the gas produced via a hyperpolarizer to obtain a polarized "gas" product. In summary, as used herein, the term "gas" has been used in certain places to descriptively indicate a hyperpolarized noble gas which can include one or more components and which may be present in one or more physical forms.

Background—Hyperpolarization

Various techniques have been employed to polarize, accumulate and capture polarized gases. For example, U.S. Pat. No. 5,642,625 to Cates et al. describes a high volume hyperpolarizer for spin polarized noble gas and U.S. patent application Ser. No. 08/622,865 to Cates et al. describes a cryogenic accumulator for spin-polarized $^{129}$Xe. The disclosures of this patent and application are hereby incorporated herein by reference as if recited in fill herein. As used herein, the terms "hyperpolarize" and "polarize" are used interchangeably and mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See U.S. Pat. No. 5,545,396 to Albert et al. The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133.

Alternatively, the noble gas may be hyperpolarized using metastability exchange. (See e.g., Schearer L D, Phys Rev, 180:83 (1969); Laloe F, Nacher P J, Leduc M, and Schearer L D, AIP ConfProx #131 (Workshop on Polarized $^3$He Beams and Targets) (1984)). The technique of metastability exchange involves direct optical pumping of, for example, $^3$He without need for an alkali metal intermediary. Metastability exchange optical pumping will work in the same low magnetic fields in which spin exchange pumping works. Similar polarizations are achievable, but generally at lower pressures, e.g., about 0–10 Torr.

Generally described, for spin-exchange optically pumped systems, a gas mixture is introduced into the hyperpolarizer apparatus upstream of the polarization chamber. Most xenon gas mixtures include a buffer gas as well as a lean amount of the gas targeted for hyperpolarization and is preferably produced in a continuous flow system. For example, for producing hyperpolarized $^{129}$Xe, the pre-mixed gas mixture is about 85–98% He, about 5% or less $^{129}$Xe, and about 1–10% $N_2$. In contrast, for producing hyperpolarized $^3$He, a typical mixture of about 99.25% $^3$He and 0.75% $N_2$ is pressurized to 8 atm or more and heated and exposed to the optical laser light source, typically in a batch mode system. In any event, once the hyperpolarized gas exits the pumping chamber it is directed to a collection or accumulation container.

A 5–20 Gauss alignment field is typically provided for the optical pumping of Rb for both $^{12}$Xe and $^3$He polarization. The hyperpolarized gas is collected (as well as stored, transported, and preferably delivered) in the presence of a magnetic field. It is preferred for $^{129}$Xe that the field be on the order of at least 500 Gauss, and typically about 2 kilo Gauss, although higher fields can be used. Lower fields can potentially undesirably increase the relaxation rate or decrease the relaxation time of the polarized gas. As regards $^3$He, the magnetic field is preferably on the order of at least 10–20 gauss although, again, higher fields can be used. The magnetic field can be provided by electrical or permanent magnets. In one embodiment, the magnetic field is provided by a plurality of permanent magnets positioned about a magnetic yoke which is positioned adjacent the collected hyperpolarized gas. Preferably, the magnetic field is homogeneously maintained around the hyperpolarized gas to minimize field-induced degradation.

Referring to the drawings, FIG. 1 illustrates a preferred xenon hyperpolarizer unit 10. As shown, the unit 10 includes a noble gas supply 12 and a supply regulator 14. A purifier 16 is positioned in the line to remove impurities such as water vapor from the system as will be discussed further below. The hyperpolarizer unit 10 also includes a flow meter 18 and an inlet valve 20 positioned upstream of the polarizer cell 22. A optic light source such as a laser 26 (preferably a diode laser array) is directed into the polarizer cell 22 through various focusing and light distributing means 24, such as lenses, mirrors, and the like. The light source is circularly polarized to optically pump the alkali metals in the cell 22. An additional valve 28 is positioned downstream of the polarizer cell 22. A more detailed explanation of the hyperpolarizer is described in Cates et al., supra, and in co-pending application to Driehuys et al., U.S. patent application Ser. No. 08/989,604, filed Dec. 12, 1997, entitled Methods of Collecting, Thawing, and Extending the Useful Life of Polarized Gases and Associated Accumulators and Heating Jackets, and identified by Attorney Docket No. 5770-4. The contents of these disclosures are hereby incorporated by reference as if recited in full herein. In order to transport the hyperpolarized gas in a gaseous state, the hyperpolarized $^{129}$Xe is preferably cryogenically accumulated in a cold finger or container 30 which is positioned in a cryogenic bath 43. The frozen polarized $^{129}$Xe gas is then thawed out of the cold finger or container 30 and captured by a collection or transport vessel 50A positioned in fluid communication with the onboard exit tap 50.

Figure 1A:
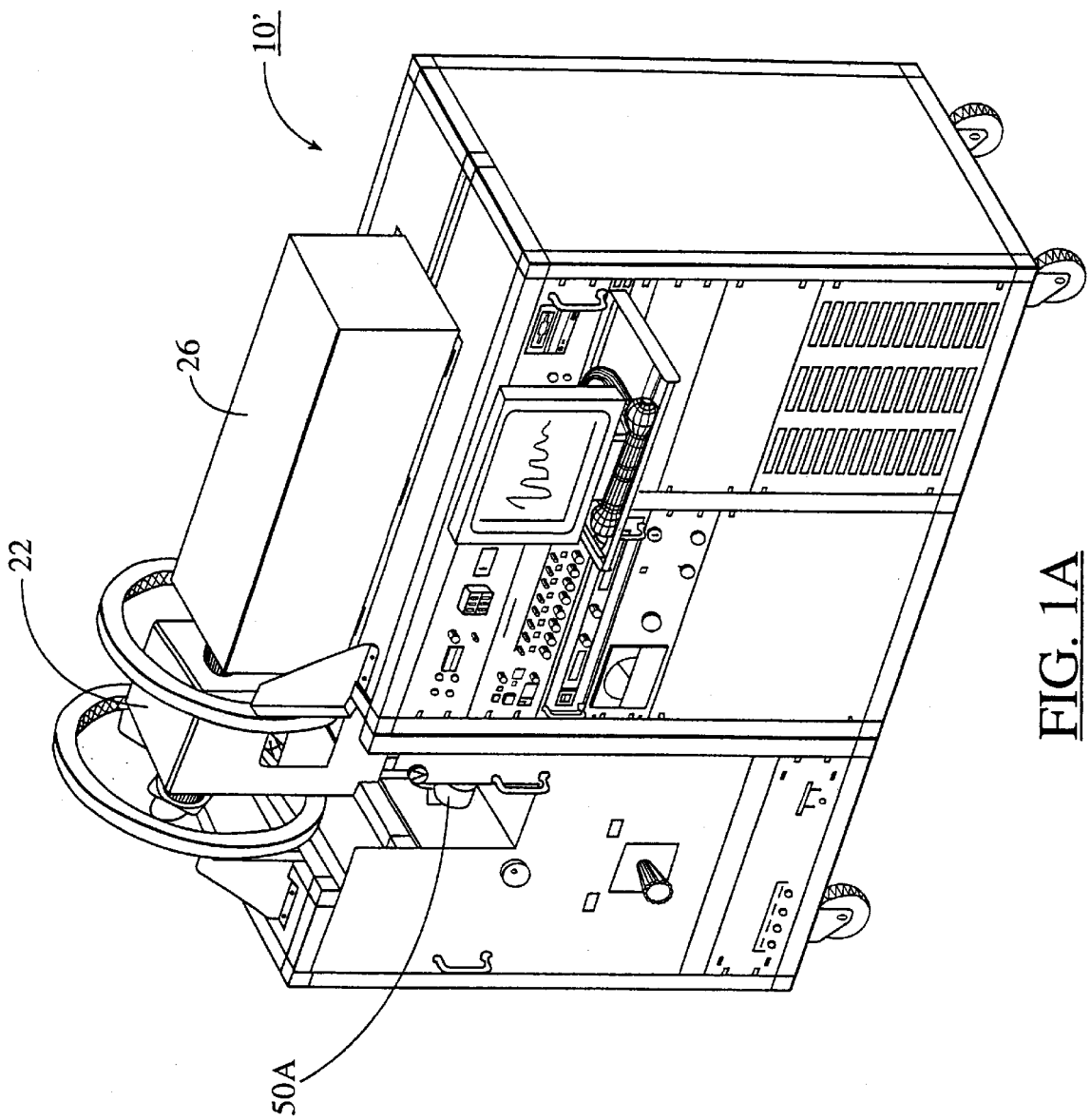
FIG. 1A is a perspective view of a helium hyperpolarizer system.

FIG. 1A illustrates a preferred helium hyperpolarizer unit 10'. Similar to the $^{129}$Xe hyperpolarizer unit 10 generally discussed above, the $^3$He hyperpolarizer unit 10' polarizes the $^3$He in a polarization cell 22 and collects the gas at the gas exit tap 50 into the storage or transport container 50A. Certain of the plumbing of the helium device differs from the xenon apparatus, because the helium is batch process unlike the continuous process used to hyperpolarize xenon.

Prior to use in the unit 10, the storage containers 50A (and other storage, transport, or collection chambers) are preferably (repeatedly) purged and/or evacuated to remove oxygen, moisture, and the like. Preferably, a rough vacuum pump is used to perform a first evacuation, then a high-purity gas is introduced into the container to purge residual contaminants. Preferably, additional evacuations are performed such that the $O_2$ concentration is about $10^{-6}$–$10^{-10}$ atm or lower. Of course, turbo-molecular pumps, cryopumps, and/or diffusion pumps (with or without heating) may also be used to treat or evacuate the vessel to remove any monolayers of moisture or water or other minute contaminants on the surface and thus further reduce contact-induced depolarization for the hyperpolarized gas.

Polarized Gas Relaxation Processes

Once hyperpolarized, there is a theoretical upper limit on the relaxation time ($T_1$) of the polarized gas based on the collisional relaxation explained by fundamental physics, i.e., the time it takes for a given sample to decay or depolarize due to collisions of the hyperpolarized gas atoms with each other absent other depolarizing factors. For example, $^3$He atoms relax through a dipole—dipole interaction during $^3$He-$^3$He collisions, while $^{129}$Xe atoms relax through N·I spin rotation interaction (where N is the molecular angular momentum and I designates nuclear spin rotation) during $^{129}$Xe-$^{129}$Xe collisions. Stated differently, the angular momentum change associated with flipping a nuclear spin over is conserved by being taken up by the rotational angular momentum of the colliding atoms. In any event, because both processes occur during noble gas-noble gas collisions, both resulting relaxation rates are directly proportional to gas pressure ($T_1$ is inversely proportional to pressure). At one atmosphere, the theoretical relaxation time ($T_1$) of $^3$He is about 744–760 hours, and for $^{129}$Xe the corresponding relaxation time is about 56 hours. See Newbury et al., *Gaseous 3He-3He Magnetic Dipolar Spin Relaxation,* 48 Phys. Rev. A., No. 6, p. 4411 (1993); Hunt et al., *Nuclear Magnetic Resonance of* $^{129}$*Xe in Natural Xenon,* 130 Phys Rev. p. 2302 (1963). Unfortunately, other relaxation processes prevent the realization of these theoretical relaxation times. For example, the collisions of gaseous $^{129}$Xe and $^3$He with container walls ("surface relaxation") have historically dominated most relaxation processes. For $^3$He, most of the known longer relaxation times have been achieved in special glass containers having a low permeability to helium. U.S. Pat. No. 5,612,103 to Driehuys et al. describes using coatings to inhibit the surface-induced nuclear spin relaxation of hyperpolarized noble gases, especially $^{129}$Xe. The contents of this patent are hereby incorporated by reference as if recited in full herein. Similarly, U.S. patent application to Deaton et al., identified by Attorney Docket Number 5770-12, supra, describes preferred gas-contact surface materials and associated thicknesses, O-ring, and valve or seal materials and/or coatings which are friendly to the polarized state of the gas, i.e., which can inhibit surface/contact-induced relaxation mechanisms.

Once the hyperpolarized gas is collected, it is typically delivered to a hospital or end user. This means that either a hyperpolarizer unit is proximately stationed in the hospital so that the hyperpolarized gas can be delivered directly to the patient, or that the gas is transported from a central, albeit remote polarization site. The remote polarization station typically requires a longer $T_1$'s relative to an onsite apparatus to allow adequate shipping and transport times. However, a centrally stationed polarizer can reduce equipment and maintenance costs associated with a plurality of on-site units positioned at each imaging site. In any case, the hyperpolarized gas is typically removed from the collection container or transport vessel and dispensed to the patient via some patient delivery system temporally limited such that the hyperpolarized state of the gas at delivery is sufficient to produce useful clinical images.

Extraction Systems

It will be appreciated by those of skill in the art that certain of the descriptions herein are primarily directed to either a liquid or a gas, but that the methods of the inventions can use multiple types of fluids and are not intended to be limited to the specific description used herein. As such, as used herein, the term "fluid" includes liquids, gases, and blends and mixtures thereof.

A. Liquid Extraction

Figure 2A:
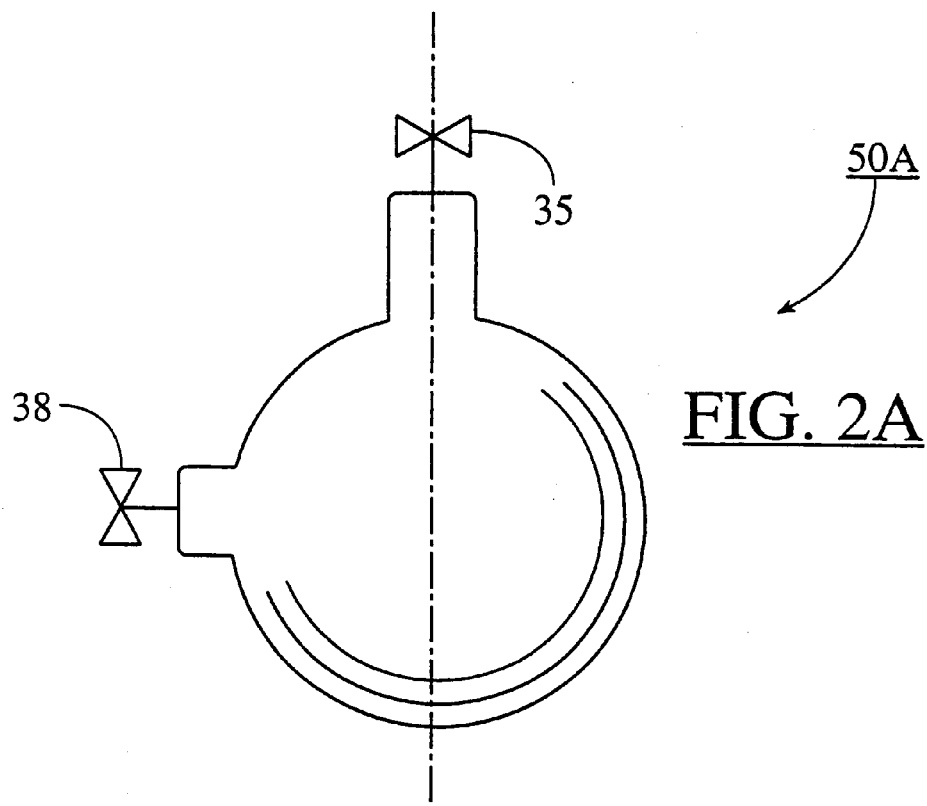
FIG. 2A is an enlarged plan view of the container shown in FIG. 1.
Figure 2B:
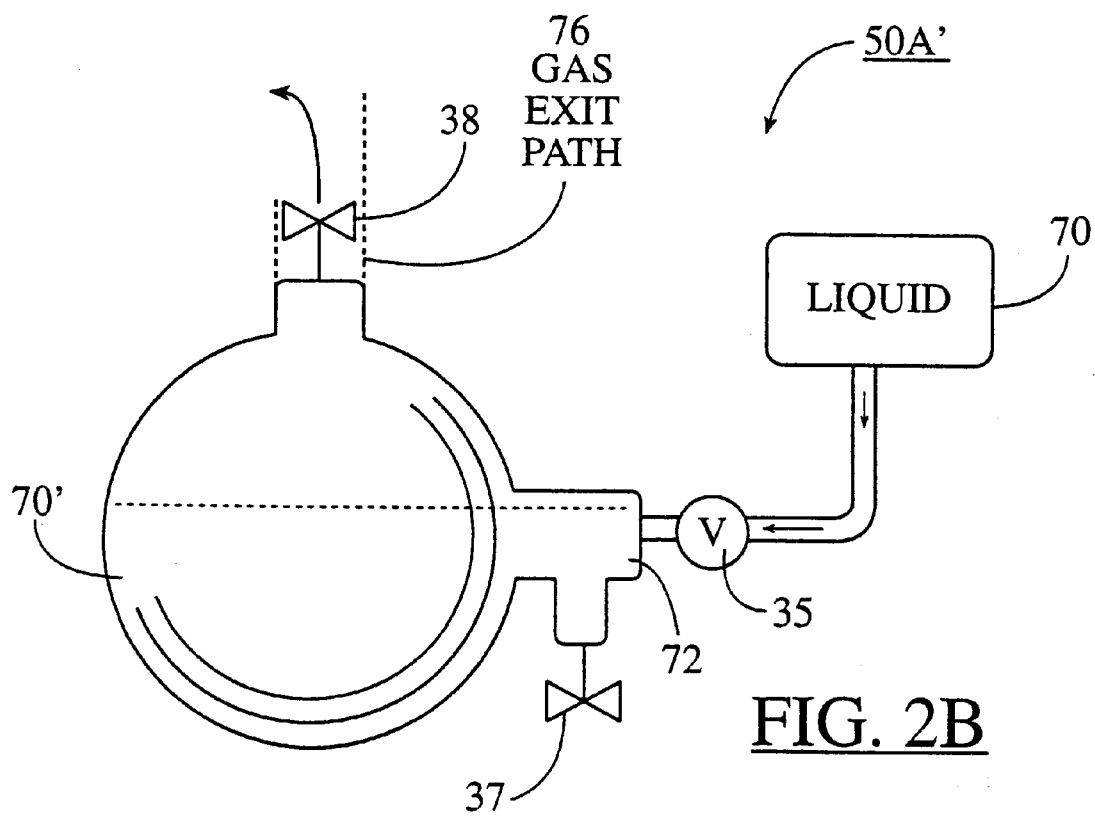
FIG. 2B is a schematic illustration of one extraction method according to the present invention showing liquid extraction of hyperpolarized gas from the container of FIG. 2A.

Turning now to the drawings, FIG. 2B illustrates one embodiment of a hyperpolarized gas extraction system according to the present invention. In this embodiment, a container 50A (FIG. 2A) is removed from the hyperpolarizer unit and transported away from the polarization site. The container is then prepared to release the gas therefrom. As shown in FIG. 2B, a liquid source 70 is attached to a liquid entry port 72. A valve 35 is opened and liquid is directed into the container 30. A valve 38 is opened to allow the hyperpolarized gas to exit the exit path 76. FIG. 2B shows an optional second valve 37 which can assist in holding degassed liquid in the container. As shown in FIG. 2B, during extraction, the container 50A is preferably oriented such that the gas exit path 76 is above the liquid entry port 72. In operation, the increasing liquid level contacts the hyperpolarized gas and pushes or forces the hyperpolarized gas out of the container 50A and into the exit path 76. It is preferred that the liquid level be adjusted so that the liquid remains in the container separate from the extracted gas, especially for gas inhalation applications. This method advantageously allows for substantially all of the hyperpolarized gas in the container 50A to be removed with minimal dilution and/or depolarization of the hyperpolarized gas.

FIG. 3 illustrates a liquid extraction system with a modified container 50A. In this embodiment, the container 50A has two ports; an inlet port 230 and an outlet port 234. As shown, the outlet port 234 is on a different (preferably opposing) side of the container and offset relative to the inlet port 230. As shown in FIGS. 6 and 9, an axis 200 drawn through the center of the container sections the container into four quadrants. Preferably, the inlet port 230 is positioned in one of the bottom quadrants and the outlet port 234 is positioned in the opposing top quadrant. Each of the ports 234, 230 is operably associated with a valve 235, 231 to control the release of the gas and introduction of the liquid, respectively. During extraction, this configuration allows the container 50A to be oriented such that the outlet port 234 is on a top end portion of the container and above the inlet port 230. As shown, the liquid source 70 preferably uses gravity to feed the liquid 70' into the container. Of course, other controlled or active feed systems can also be employed (such as pumps, compression cuffs, syringes, and the like).

Referring again to FIG. 3, as illustrated, the inlet port 230 includes a connector 232 which allows the liquid source 70 to be attached to the container 50A. Similarly, the outlet port 234 includes a connector 236 which can attach to a patient delivery vessel 250. The patient delivery vessel 250 is preferably a collapsible bag. Of course, as an alternative to a patient delivery vessel 250, the gas can be directly routed from the outlet port/exit path 234 to the patient (such as to an inhalation mask positioned over a patient's nose/mouth FIG. 13, 255).

Figure 4:
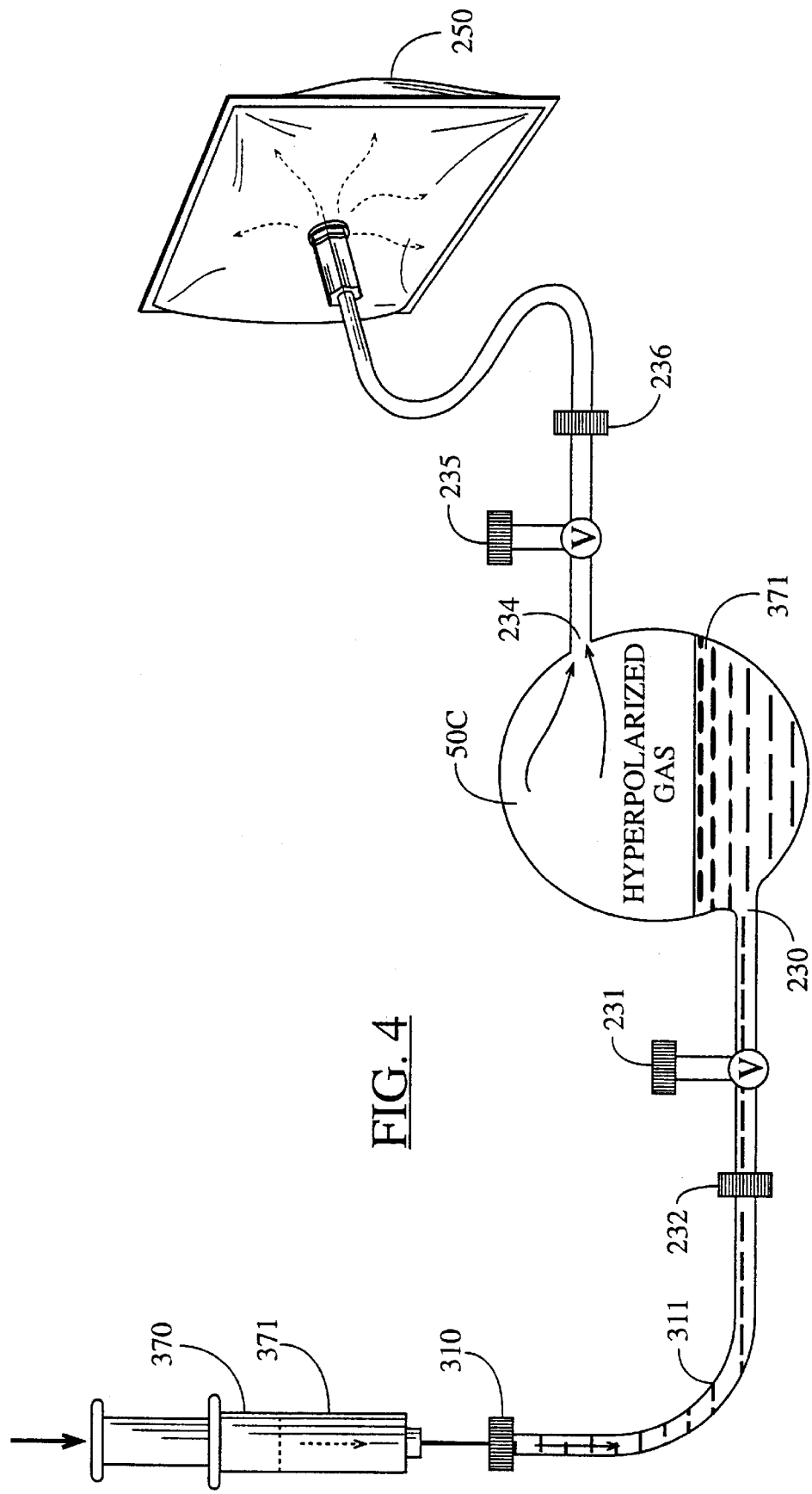
FIG. 4 is a schematic illustration of a liquid extraction system showing an alternative liquid source according to another embodiment of the present invention.

FIG. 4 shows another embodiment of a liquid extraction system. In this embodiment, the liquid source 370 is a syringe. As such, the extraction liquid 371 is inserted/injected via the syringe 370 into an access port 310 positioned in fluid communication with the container 50C. As shown, the access port 310 is positioned in an elbow 311 which is in fluid communication with the gas in the container 50C and is configured to receive a portion of the syringe therein. Preferably, the access port 310 is resilient in that it is configured with resilient material to receive the septum therein in a manner which provides an air tight seal. In one embodiment, the access port 310 is a lure-type connector. Also, preferably the access port is self-healing such that it forms an air-tight seal with the syringe when inserted therein and automatically collapses or closes to seal the port when the syringe 370 is withdrawn.

As noted, the liquid contacts the hyperpolarized gas. As such, for in vivo applications, it is preferred that the extraction liquid be selected so as to be non-toxic and non-depolarizing to the hyperpolarized gas. It is further preferred, for liquids which have a relatively high oxygen solubility value, that the liquid be processed to be more compatible to the hyperpolarized gas. For example, it is preferred that the liquid be at least partially de-oxygenated and/or partially de-ionized prior to introduction into the container or transport vessel with the hyperpolarized gas. It is more preferred that the liquid be sterilized and substantially de-oxygenated and/or substantially de-ionized. Other modifications and treatment processes can also be performed on the liquids to make them more polarization friendly. For example, certain elements of the liquids can be substituted or deuterated and the like. It is additionally preferred that the liquid be selected such that the hyperpolarized gas is substantially insoluble in the liquid. It is preferred that the solubility of the hyperpolarized gas in the fluid be less than about 0.2. For example, xenon has a solubility of about 0.14 in $H_2O$ (with helium being about 0.01). In contrast, for example, xenon has a solubility of about 2.0 in hexane making this a poor choice for an extraction fluid for this gas (even aside from its toxicity issues).

Of course, a plurality of liquids can also be used as the extraction liquid, such as a liquid mixture, or blend whether miscible or immiscible. Tests indicate that one suitable liquid is water. Water is compatible and substantially non-depolarizing to both $^3$He and $^{129}$Xe.

Figure 5:
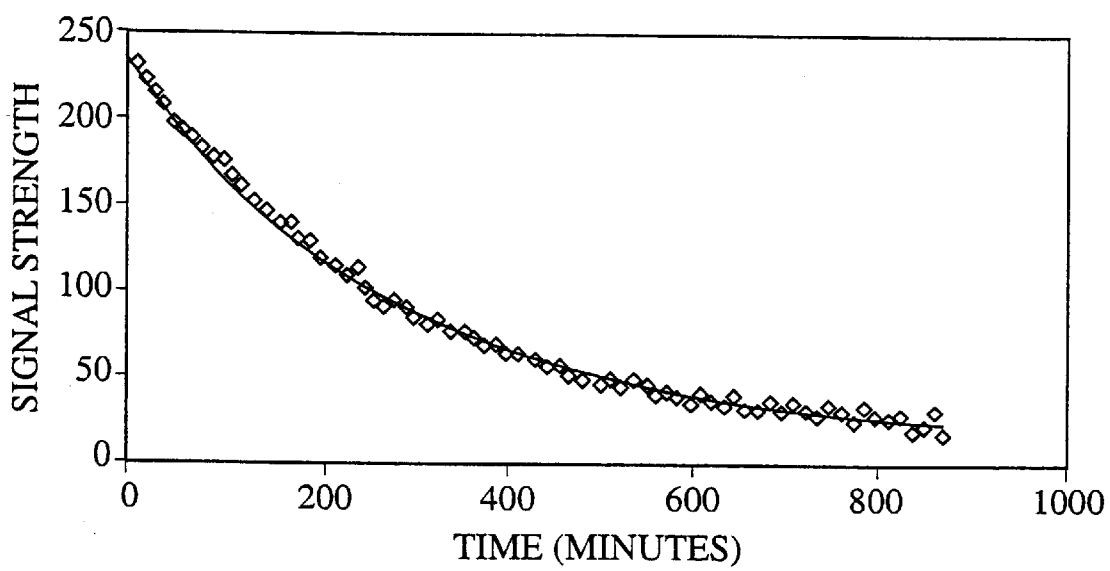
FIG. 5 is a graphical representation showing the signal strength of hyperpolarized $^3$He over time (the exponential decay constant of the gas) after contact with water.

In one example, adding about 20 cubic centimeters of partially degassed water into the chamber of a 250 ml container changed the associated $T_1$ of the gas in the container from about 8 hours to about 5 hours. As shown in FIG. 5, the polarization decay curves observed from this test fit the exponential decay curve. This test supports the suitability/viability of this active extraction system. Preferably, immediately after the extraction is completed (especially when used with $^3$He), the extracted hyperpolarized gas maintains a $T_1$ equal to at least about 80% or more, most preferably, 90% or more of the value of the $T_1$ immediately prior to initiation of the extraction method (assuming a properly processed, cleaned, and appropriate transfer container).

B. Liquid as a Masking Agent

An additional aspect of the present invention is directed to using liquid as a masking agent in physical systems or containers which potentially contact the hyperpolarized gas. As is now understood, the effective $T_1$ of gas in a container is additive in relationship to the materials that the gas contacts. That is, the effective $T_1$ will increase nonlinearly according to the following equation.

$$1/T_{1\ chamber} + 1/T_{1\ material} = 1/T_{1\ effective} \qquad \text{Equation 1.0}$$

Therefore, the effective $T_1$ is dependent on the chamber surface area and material, as well as any other materials which contact the gas. By inhibiting the gas from contacting degrading materials, the effective $T_1$ can be extended or preserved.

Figure 6A:
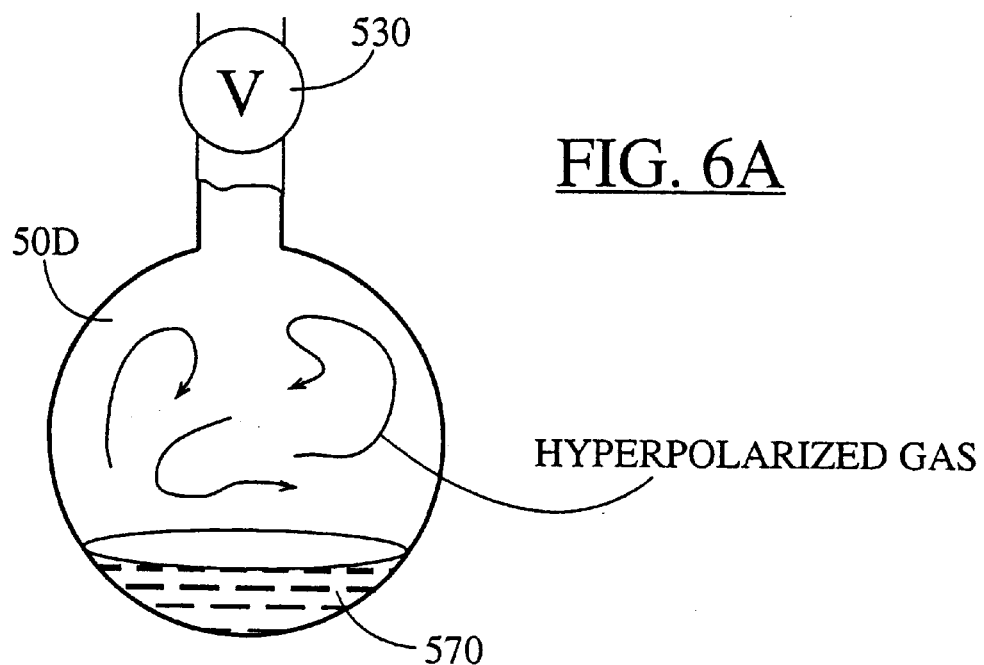
FIG. 6A is a schematic representation of a container with liquid inserted therein in accordance with a masking method of one embodiment of the present invention.
Figure 6B:
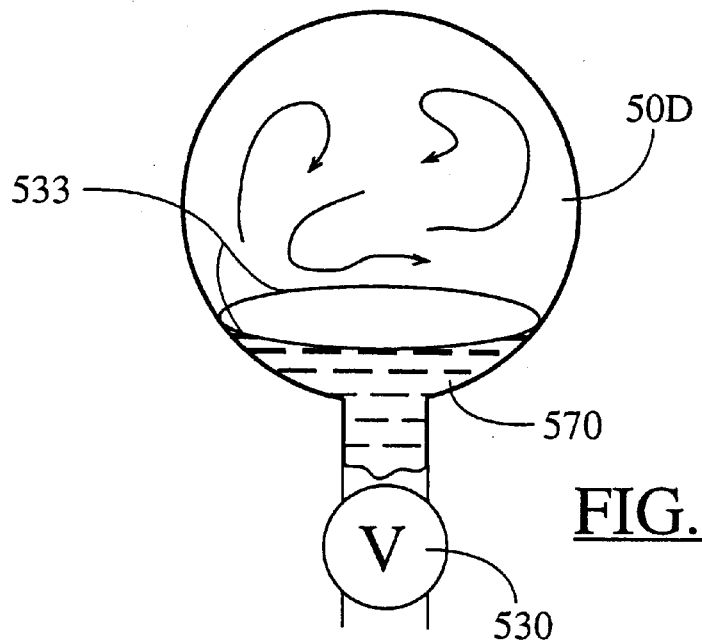
FIG. 6B is a schematic representation of the container of FIG. 6A, showing the container oriented to dispose the liquid over the neck (valve area) of the container according to one embodiment of the present invention.

As shown in FIG. 6B, a (predetermined) exposed internal surface 533 of the container 50D is covered with liquid. Preferably, the liquid 570 is selected such that it displays a greater compatibility with the hyperpolarized gas than the degrading contact surface or component (such as conventional O-rings, valves, seals, and the like) and is introduced into the container 50D to inhibit direct contact between the undesirable surface and the hyperpolarized gas. Advantageously, other properties typically attributed to the undesirable surface (seals, etc.) can be retained. Further, if used as shown to mask seals and the like, commercially available seals can be used without requiring specialized (and potentially costly) formulations of materials. This is because the liquid (or fluid) covers the surface or component, thereby masking the potentially depolarizing area from the hyperpolarized gas by contacting the gas with a material which has improved relaxivity relative to the undesirable surface or component. Also preferably, the liquid is chosen such that it is substantially non depolarizing to the hyperpolarized gas (and resistant to hyperpolarized gas dissolution therein), so that it increases the length of the polarized life of the gas in the container over the life of the gas without the liquid mask. As discussed above, the liquid is also preferably non-toxic in that it contacts the (in a preferred embodiment, inhalable) hyperpolarized gas. For liquids which have high oxygen solubility, it is preferred that the liquid be at least partially de-oxygenated/de-ionized as discussed above. Further, one or more liquids can be used and the liquids may otherwise or additionally modified or processed as described above.

In operation, as shown by FIGS. 6A and 6B, a quantity of liquid is placed in the container 50D housing the polarized gas. The container 50D is then oriented such that the liquid in the container covers and thus inhibits the gas from contacting the valve 530 or other undesirable material or component, i.e., is positioned intermediate of the gas and the valve to mask the valve from the polarized gas. For example, in one test, fifteen cubic centimeters of de-ionized/de-oxygenated water were injected into a one-liter plastic bag with a valve thereon that had been previously filled with polarized gas. The bag was then positioned such that the water in the bag completely masked the valve from the polarized gas. The addition of water to the plastic bag increased the $T_1$ by about one hour.

C. Extraction Using a Gas

In this embodiment, a second gas is used to transfer the hyperpolarized gas from one vessel to another. Inasmuch as a preferred embodiment of the liquid transfer was described above, this description will be directed to the use of an extraction gas or extraction gas mixture (a plurality of gases) to transfer the hyperpolarized gas out of a container or transport vessel.

Figure 7:
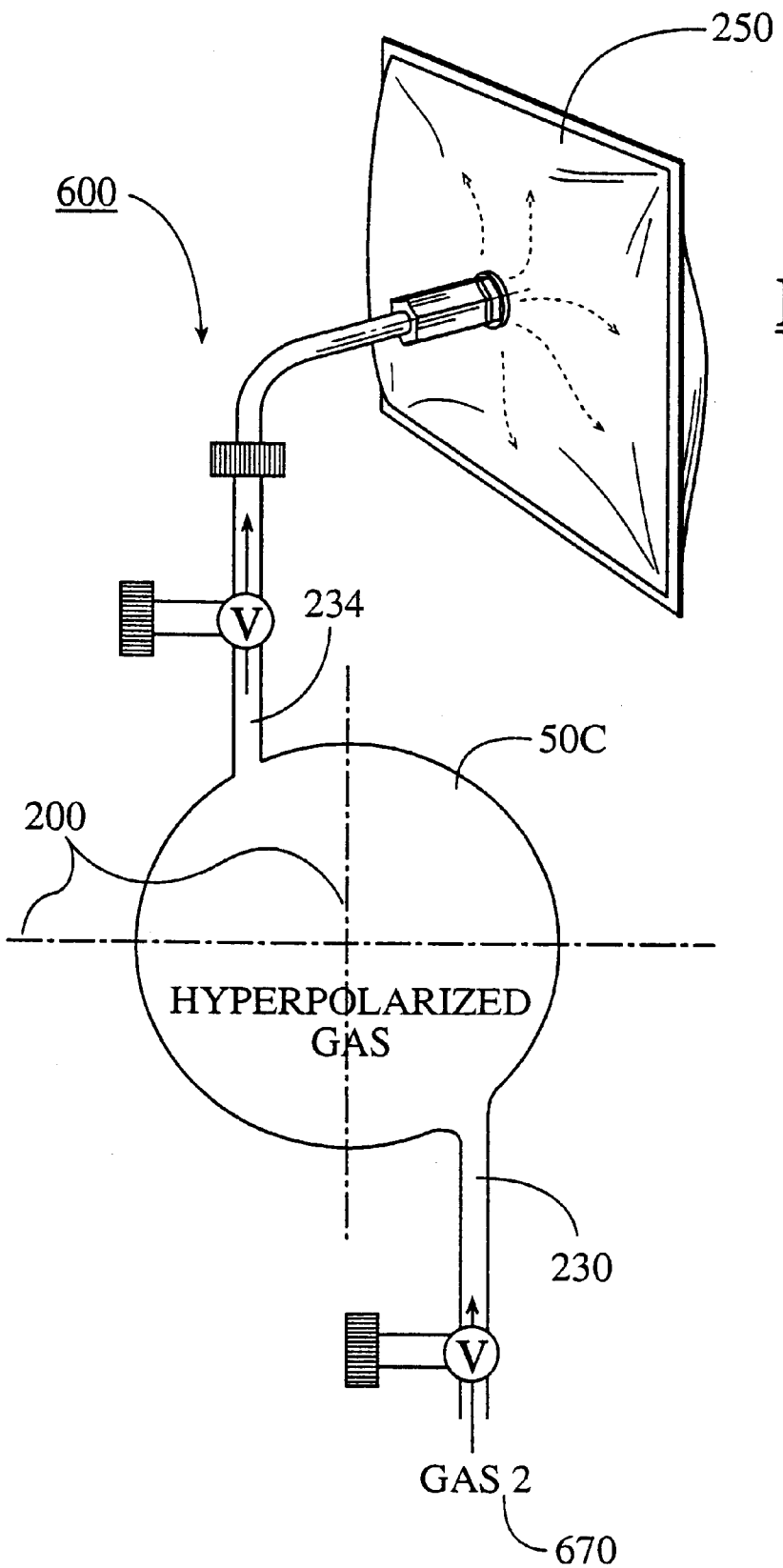
FIG. 7 is a schematic representation of a gas extraction method according to one embodiment of the present invention.
Figure 8:
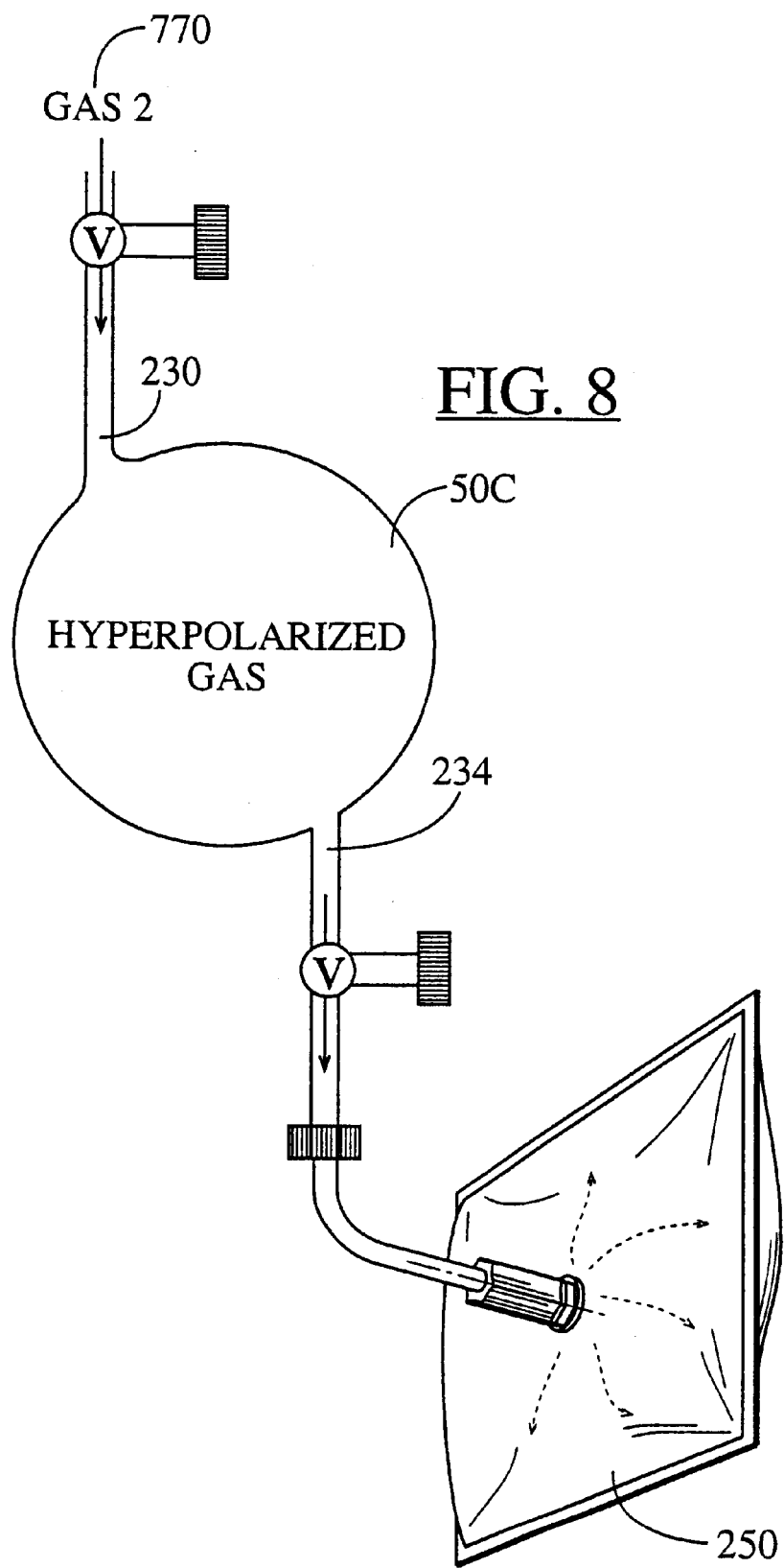
FIG. 8 is a schematic representation of a gas extraction method according to another embodiment of the present invention.

Turning now to FIGS. 7 and 8, two embodiments of a gas extraction system 600, 700 are shown. In these embodiments, the container 50C is the same as that described above, although, of course, the method and containers contemplated by this invention are not limited thereto. As shown, the container 50C includes the inlet and outlet ports 230, 234, respectively. In this embodiment, the extraction gas 670 is introduced into the inlet port 230 to contact the hyperpolarized gas in the container and force the gas out of the container through the outlet or exit port 234. As the extraction gas 670 contacts the hyperpolarized gas, it is preferred that it is non-toxic (so as not to contaminate the hyperpolarized gas) and substantially non-depolarizing to the hyperpolarized gas. Preferably, the second gas or extraction gas (or gas mixture) 670 has a substantially different density relative to the hyperpolarized gas. For example, $N_2$ would be suitable to use with both $^3$He and $^{129}$Xe because it is inert, non-toxic, and its density is higher than that of $^3$He and lower than that of $^{29}$Xe. Alternatively, helium is also inert and non-toxic and can be used to extract the $^{129}$Xe. In any event, it will be appreciated by one of skill in the art that at 20° C., helium has a density of about 0.17 g/l, xenon about 5.49 g/l and, $N_2$ about 1.17 g/l and as such, these density variations allow the successful extraction of the hyperpolarized gas according to the present invention.

In one embodiment, as shown in FIG. 7, the hyperpolarized gas is $^3$He which is a relatively light gas (low density). As such, the extraction gas 670 is fed into the bottom of the container and the increasing volume of the extraction gas into the container 50C forces the lighter weight gas ($^3$He) to exit the top of the container through the exit port 234 into a collection vessel 250 or delivery site. In contrast, as shown in FIG. 8, the hyperpolarized gas is $^{129}$Xe, which is a relatively heavy gas (high density). As such, the extraction gas 770 is introduced into the top of the container and forces the heavy hyperpolarized gas out of the bottom through the exit port 234. In one embodiment, the extraction gas 670, 770 is introduced at a rate and in a way which allows it to contact the hyperpolarized gas at a front boundary plane but remain substantially independent of the hyperpolarized gas as the hyperpolarized gas is pushed/forced out of the container (i.e., the gases remain substantially unmixed). In another embodiment, the extraction gas 670, 770 is introduced to mix with the hyperpolarized gas to form a gas mixture—preferably by the time the gas reaches the exit port 234. The amount of hyperpolarized gas in the mixture is preferably such that the mixture provides a sufficient amount of the hyperpolarized gas for signal imaging (for useful MRI clinical images) and is suitable for patient inhalation. Preferably, for this embodiment, the container is configured and sized to provide at least one patient-inhalable dose of the hyperpolarized gas mixture. It is also preferred that the container be configured with the ports 230, 234 positioned on opposing sides or ends of the container and offset (side to side) relative to the other. As shown, the inlet and outlet ports 230, 234 are positioned on opposing sides of the centerline of the container and more preferably on opposing sides and ends (opposing quadrants) of a two-dimensional axis 200 drawn through the center thereof (see FIG. 7).

D. Mechanical Extraction

In this embodiment, mechanical extraction means such as pumps (diaphragm, rotary, or centrifugal pumps) or other mechanical devices are employed to act as a gas transfer source to pull or extract the hyperpolarized gas from the container in a manner which is minimally depolarizing to the hyperpolarized gas. If pumps or other active mechanisms are employed, preferably the gas contact surfaces and components of the devices are masked to inhibit direct contact with the hyperpolarized gas, as described above, and/or, alternatively, formed or coated from hyperpolarization-friendly materials.

1. Syringe Extraction

Figure 9A:
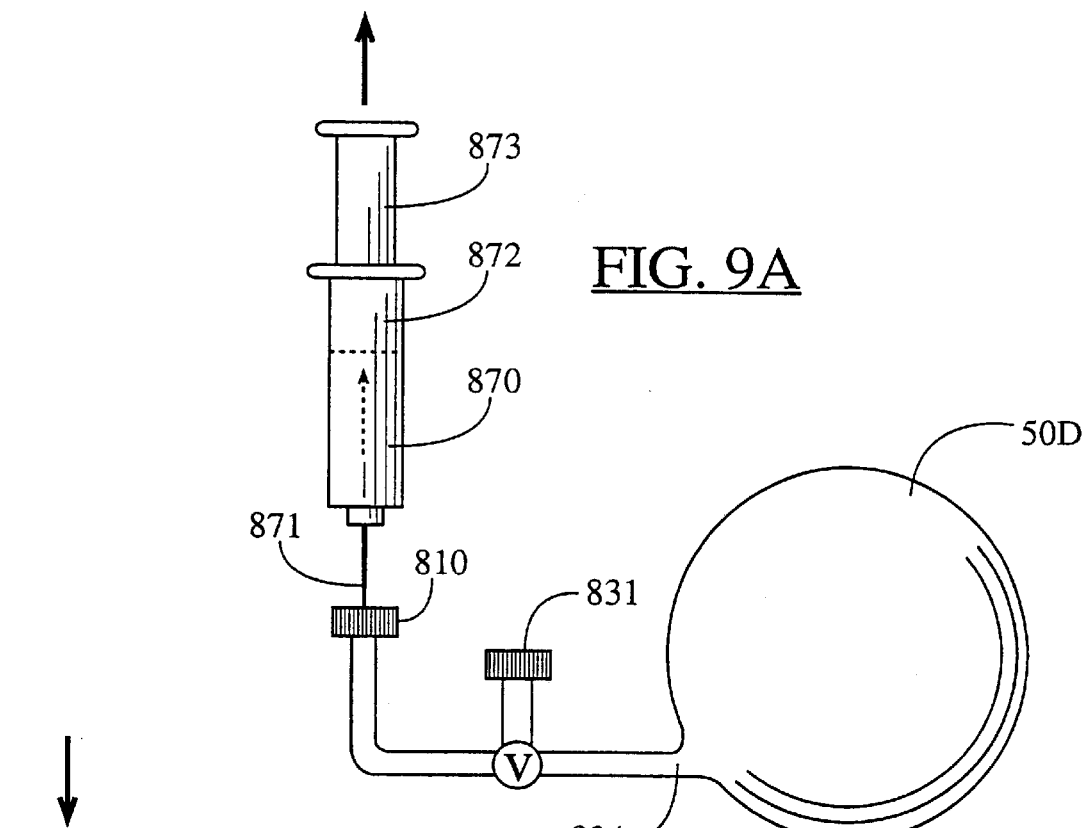
FIG. 9A is a schematic illustration of a gas extraction method and associated components according to one embodiment of the present invention.
Figure 9B:
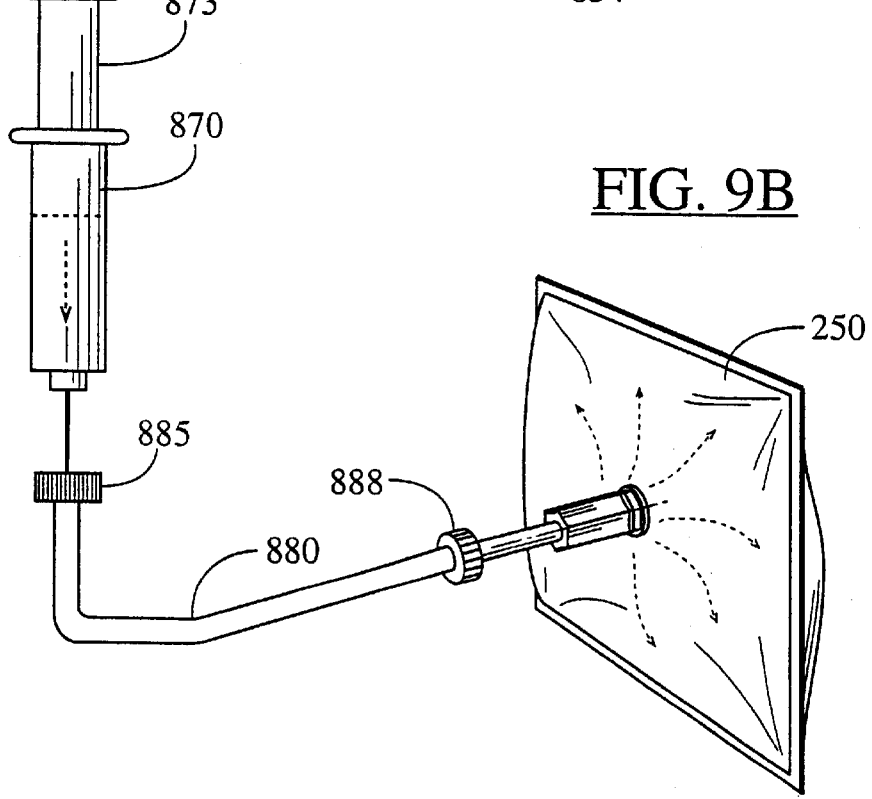
FIG. 9B is a schematic illustration of the release/delivery of the gas extraction method shown in FIG. 9A.

In a preferred embodiment, as shown in FIGS. 9A and 9B, a gas-tight syringe 870 is introduced into the container or transport vessel 50D such that it is in fluid communication with the hyperpolarized gas therein. Preferably, the syringe 870 enters the container through an externally accessible port 810 which is configured to provide the gas-tight (and air-tight) seal. Suitable seal configurations include septum and lure-type connectors. As shown in FIG. 9A, the container 50D preferably includes a valve 831 positioned intermediate the chamber 834 and the access port 810 for helping facilitate the integrity of the seal 810 during increased pressures sometimes experienced by the container during shipping and storage. In operation, the valve 831 is opened, one end of the syringe 871 is introduced into the access port of the container 810 and a controlled quantity of hyperpolarized gas is withdrawn into the chamber 872 of the syringe (pulled out) upon retraction of the plunger 873 therein. The hyperpolarized gas is then enclosed in the syringe 870 and can conveniently be discharged into the patient delivery unit (such as an inhalation mask) or into another delivery vessel such as a collapsible bag 250 as shown in FIG. 9B. Preferably, the syringe 870 is formed from a polymer or coated with a polymer or high purity metal coating on the gas contact surfaces to inhibit or minimize any depolarization attributed thereto. Also preferably, the syringe 870 is pre-conditioned to de-oxygenate the residual gas in the chamber 872 such as by evacuating and purging as described above. See also U.S. Patent Application identified by Attorney Docket No. 5770-12, the contents of which were incorporated herein by reference as stated above.

As illustrated by FIG. 9B, to deliver or discharge the hyperpolarized gas, the syringe 870 is preferably inserted into a port which is positioned in communication with the patient delivery vessel 250. The plunger of the syringe 873 is depressed and the gas is "pumped" out of the syringe and discharged into the patient delivery vessel 250. Similar to the access port 810 above, the delivery access port 885 preferably forms an airtight seal with the syringe 870 to introduce the hyperpolarized gas into the container/port 885 without contaminating the hyperpolarized gas sample with oxygen.

As shown by FIG. 9B, a coupling member 880 is configured to provide the sealed pathway to deliver the gas from the syringe 870 to the deliver container 250. The coupling member 880 provides the path connections 885, 888 to the syringe 870 and the patient delivery vessel 250 or inhalation mask (FIG. 13, 255) respectively. Although not shown, valves and other seal arrangements can also be employed as discussed above. Advantageously, this method allows controlled amounts of the gas to be introduced into the delivery device/vessel, thereby allowing more precise amounts of hyperpolarized gases to be transported, which in turn, reduces residual waste caused by unused gas left in the container. Further, controlled delivery and extraction allows a more predictable delivery dosage and potentially decreases product costs over that of typical conventional systems.

2. Inflatable Extraction

Figure 10:
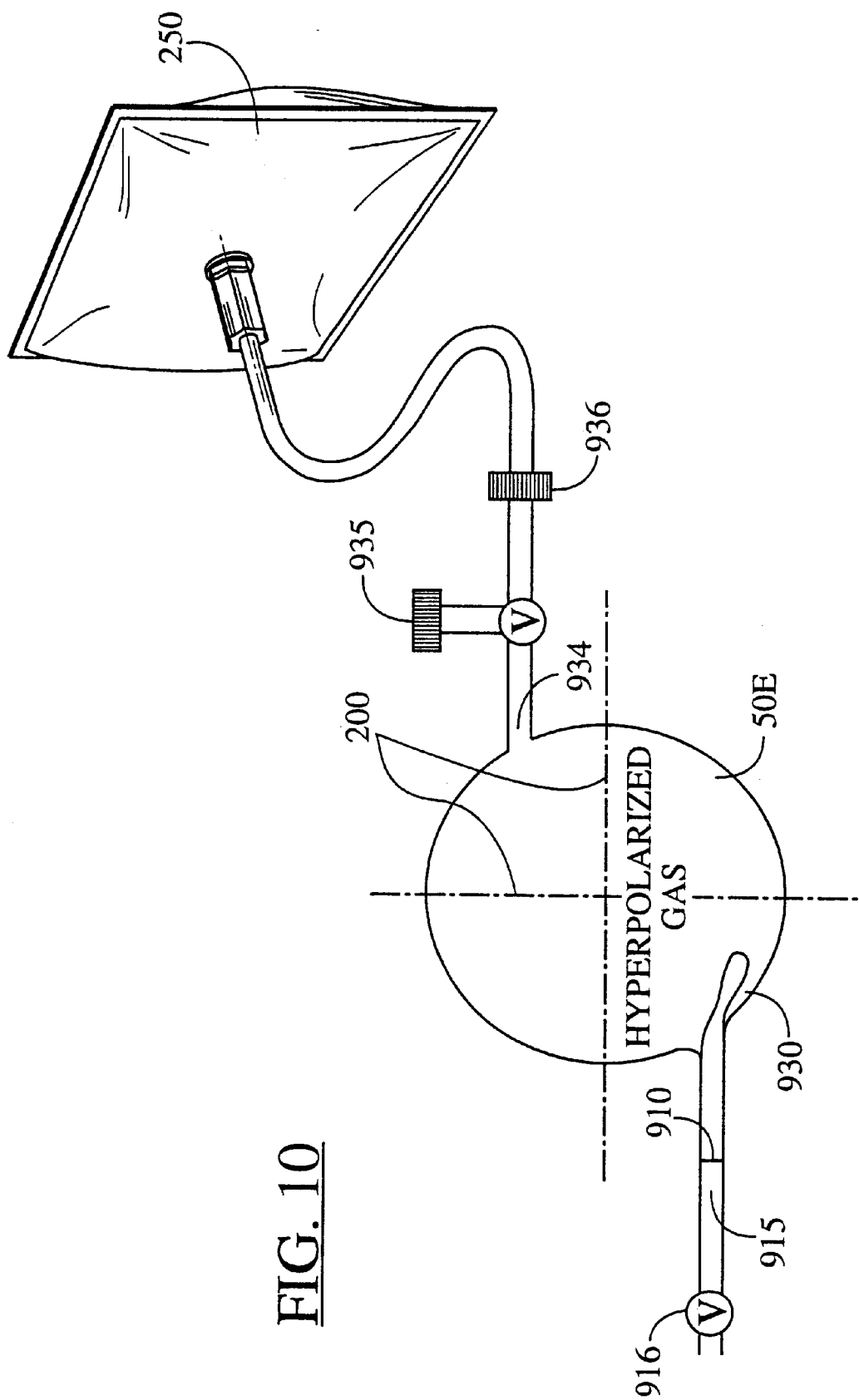
FIG. 10 is a schematic representation of a container with a resilient member and an associated expandable material extraction method according to one embodiment of the present invention.
Figure 11:
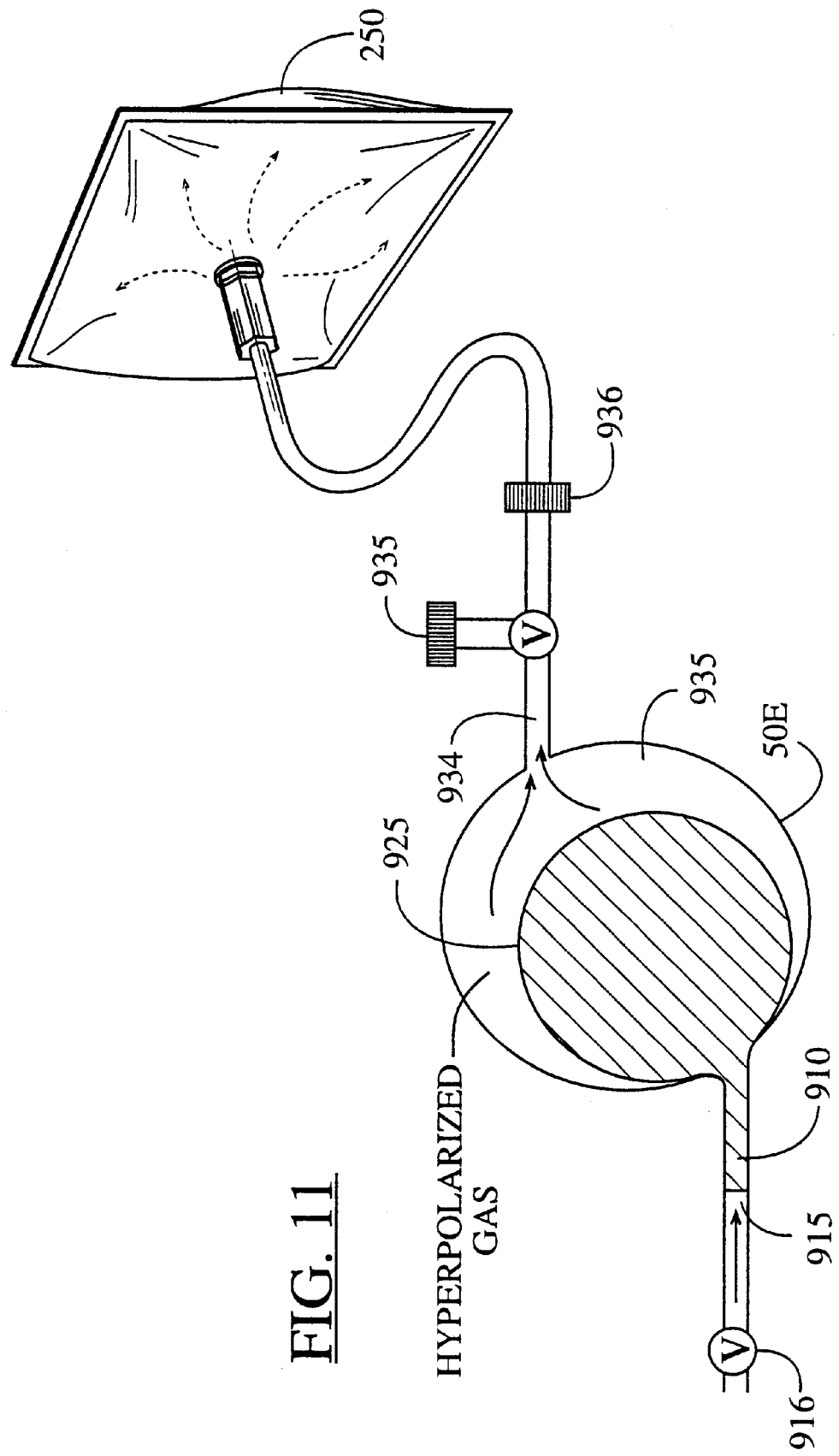
FIG. 11 is a schematic representation of the method and container in FIG. 10 showing the resilient expandable member in the container in an expanded position in the container.
Figure 12:
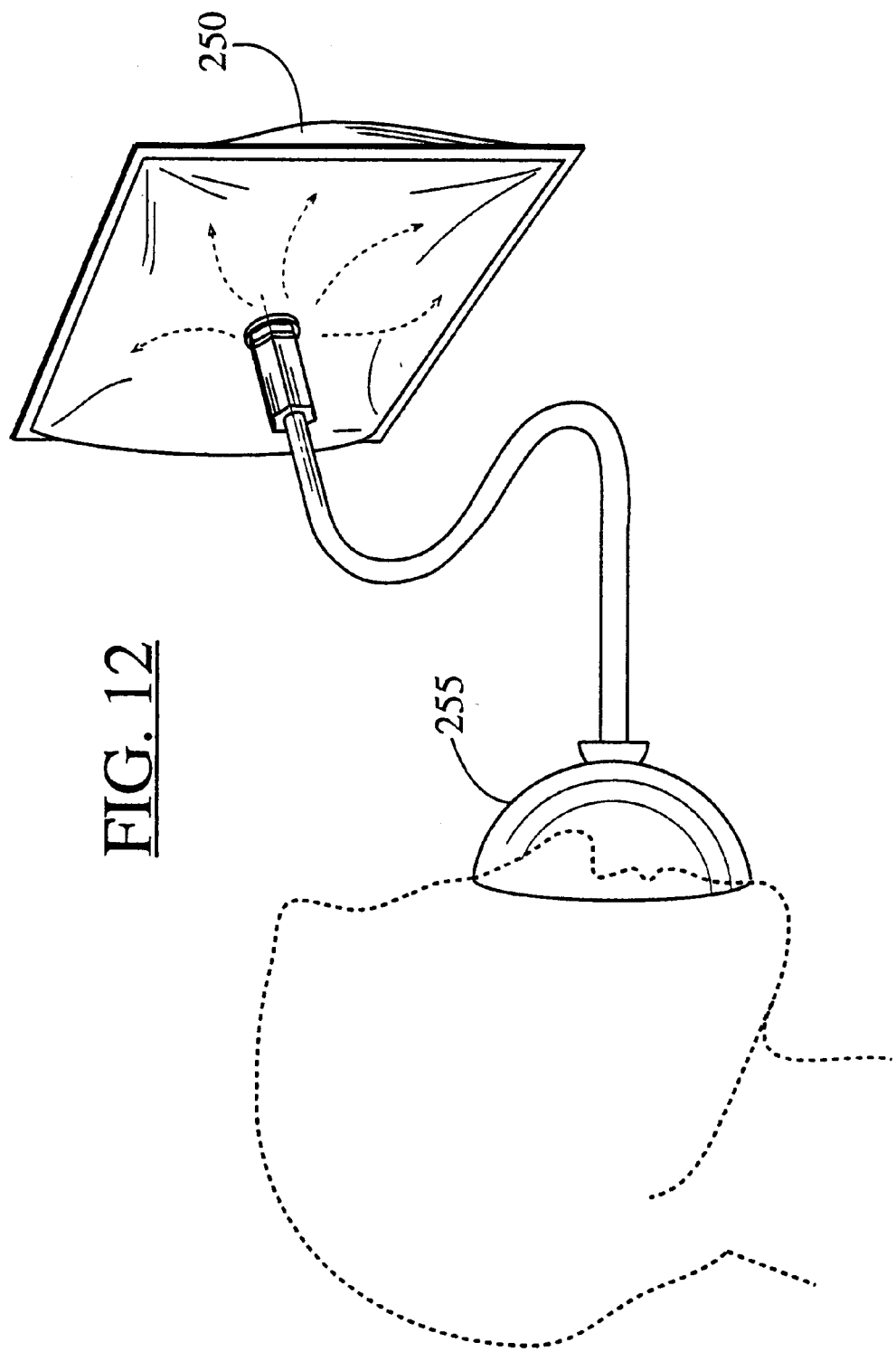
FIG. 12 is a schematic illustration of a patient delivery system according to the present invention, the hyperpolarized gas being directed from the deliver vessel to an inhalation mask positioned on a patient.

FIGS. 10 and 11 illustrate another embodiment of the present invention. The container 50E includes a resilient member 910 positioned in the container 50E such that it is in fluid communication with the hyperpolarized gas in the container. In operation, the resilient member 910 expands from a first position (shown in FIG. 10) to a second position (shown in FIG. 11). Thus, the expanded resilient member 910 translates a further distance or depth into the container to expel the hyperpolarized gas out of the exit port 936 into the delivery path or patient delivery vessel 250. The expansion is responsive to fluid introduced into the fluid entry port upstream of the container. As shown, the resilient member 910 is positioned intermediate the fluid entry port 915 and the hyperpolarized gas in the container 50E. The exit port/path 934 of the container 50E is preferably positioned opposing the inlet port 915 as described for the liquid extraction method above. As shown in FIG. 11, the collapsed resilient member 910 extends a small.

Preferably, the resilient member 910 is securely attached to the container such that it forms a fluid-tight seal around the walls or circumference of the inlet port 915. A valve 916 can be positioned upstream of the resilient member to minimize oxygen entry into the container. As shown in FIG. 11, this sealed attachment will permit the resilient member to act as a barrier surface 925 to contain the fluid(s) introduced to expand the resilient member 910 separate and apart from the hyperpolarized gas. Alternatively, the resilient member 910 can be configured to expand with fluid introduced therein, while also letting a portion of the expansion fluid enter the container 50E downstream of the resilient member 910 to form a gas mixture as was described for the gas extraction method above. For example, an expansion gas comprising nitrogen can be introduced into the fluid entry port 915 and used to inflate the resilient member 910. The resilient member 910 can include apertures or be secured to the container in a way to define apertures to allow a portion of the nitrogen to pass therethrough (not shown). The nitrogen and hyperpolarized gas are then pushed out of the exit port 934 by the inflated positions of the resilient member 910.

In any event, as the resilient member barrier surface 925 contacts the hyperpolarized gas, it is preferred that it be formed from a polarization-friendly material (or coated with same) so as to inhibit contact induced polarization attributed thereto.

Figure 13:
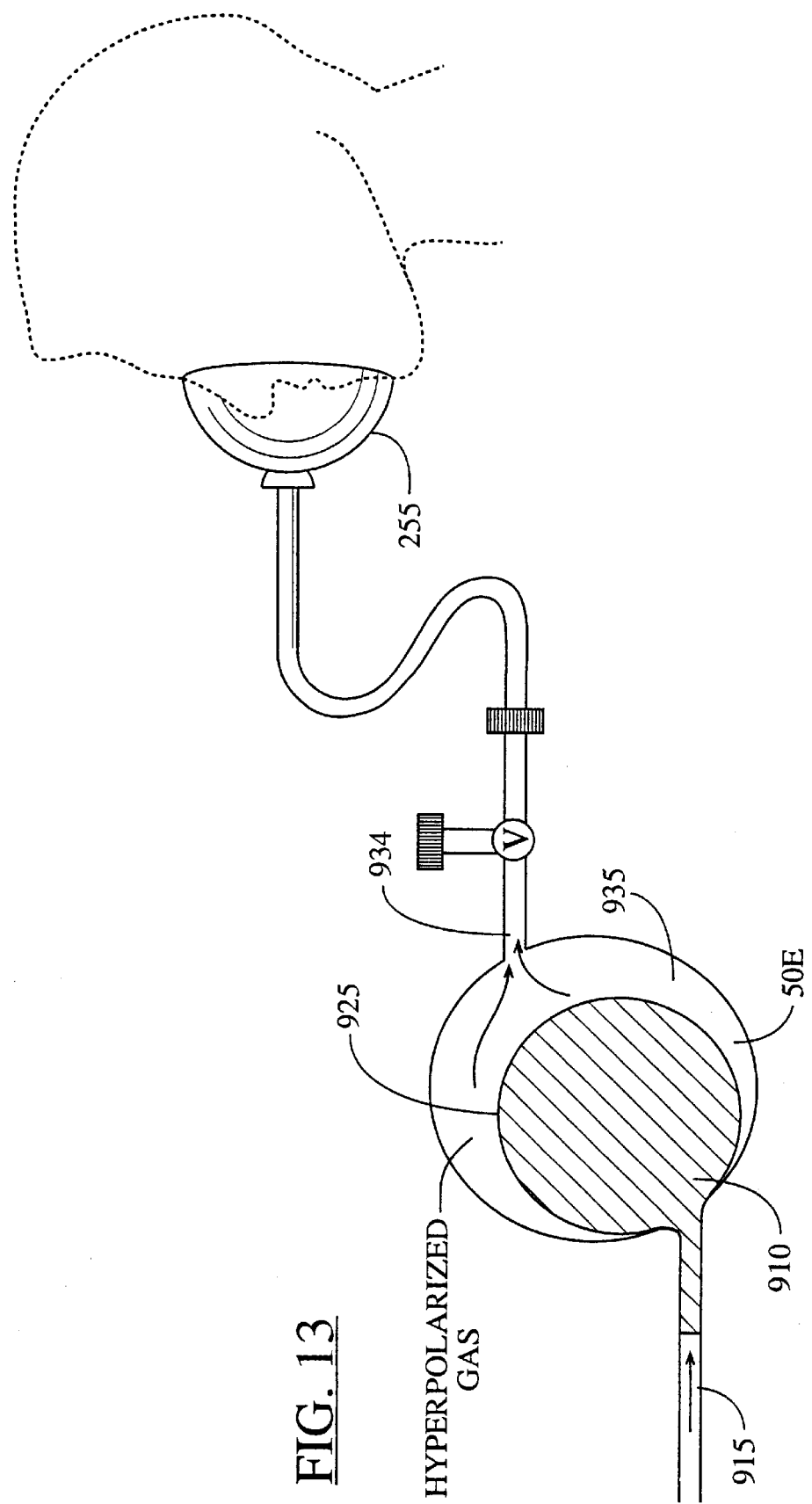
FIG. 13 is a schematic illustration of a direct delivery method using the gas extraction method shown in FIG. 11.

Once the hyperpolarized gas has been extracted from the transport vessel it can be captured in a patient delivery system such as a collapsible bag 250 as shown in FIG. 11. The bag can be conveniently compressed to force the hyperpolarized gas into an inhalation mask 255 positioned on a subject. Alternatively, the hyperpolarized gas can be extracted as described herein, but delivered directly to the subject as illustrated in FIG. 13.

E. High Efficiency Transport Vessel

In one embodiment, which can reduce the need for an active or mechanical secondary means of extraction, the container itself can be alternatively configured to reduce the amount of gas remaining in the vessel over conventional vessels. In this embodiment, a low volume, high pressure transport vessel is configured to transport hyperpolarized gas. Even without a secondary means of mechanical extraction, the gas in the container can be released to stabilize with atmospheric pressure as described for conventional extraction methods. However, because containers with smaller chambers are used, a lesser volume of gas remains in the chamber at the 1 atm condition compared to larger low-pressure transport vessels.

In a preferred embodiment, the container is sized and configured to be 500 cc's (cubic centimeters) or smaller, and pressurized to about 3–10 atm of pressure. For $^3$He, the container is preferably sized to be less than about 200 cc's and pressurized at about 5–10 atm. More preferably, the $^3$He container is sized at about 200 milliliters or less, and pressurized to about 6–10 atm. This will allow an equivalent gas content of about 1.2 liters, which allows a full one liter to be extracted just by opening the valve to equalize to ambient pressure at the desired delivery point.

In another embodiment, the transport container 22 according to the present invention can be configured to act as the polarization chamber (FIG. 1, 22). In this embodiment, the transport container is the polarization chamber 22 and is detachable from the hyperpolarizer 10 (not shown). Thus, the transport container can be configured as a dual purpose vessel to allow polarization and still be configured to be a transport container as described hereinabove; this configuration can reduce the number of gas transfers, thereby improving the transfer efficiency and reducing the amount of residual gas that is wasted.

F. Cryo-Cooled Gas Extraction

Figure 14:
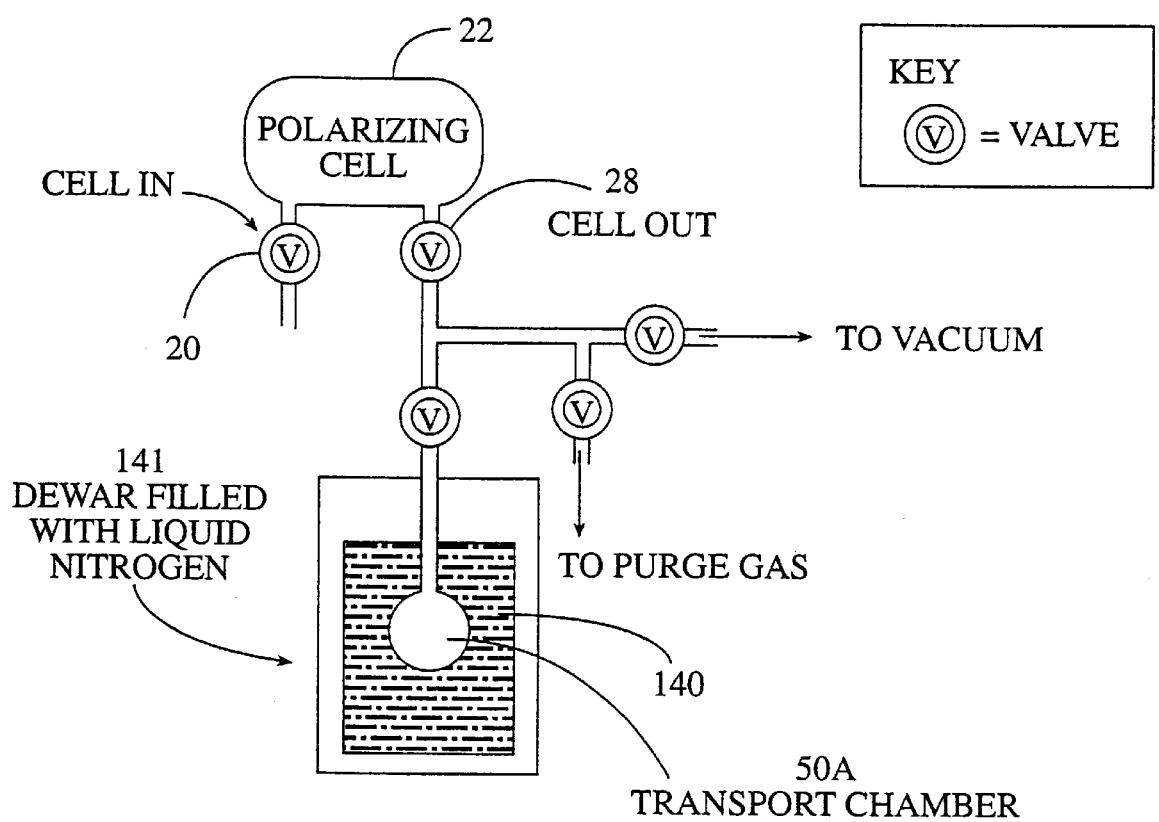
FIG. 14 is a schematic illustration of a cryogenic cooling method according to the present invention.

FIG. 14 illustrates yet another aspect of the present invention. This figure illustrates one embodiment of an improved transfer method according to the present invention. More particularly, this figure shows cooling the container 50A to a desired temperature (preferably below the freezing point of water, i.e., sub-zero temperatures). More preferably, the container is cooled to at least about 195° K. (such as by exposing the container to a dry ice ($CO_2$). Most preferably, the cooling is carried out by exposing the container or chamber to cryogenic temperatures, such as to liquid nitrogen or liquid helium temperatures. For example, as shown in FIG. 14, the cooling is performed by exposing the container 50A to a liquid nitrogen bath (77° K.) 140. In this figure, a dewar 141 is configured to hold a quantity of cooling liquid and the container 50A is at least partially immersed therein. Although illustrated as immersed, the invention is not limited to thereto. The dewar 141 can be alternately configured to receive only a portion of the container therein, or to have a smaller amount of cooling liquid therein. In addition, of course, other cooling means can be used which are known to those of skill in the art including but not limited to refrigeration systems, ice baths, other cryogenic exposure techniques and the like, to cool the container to a desired temperature. In operation, the hyperpolarized gas exits the polarizer cell 22 and enters the cooled transport container chamber. The cooled walls of the container allow increased volumes of hyperpolarized gas in the chamber (compared to non-cooled chambers) thereby increasing the quantity of hyperpolarized gas captured therein. Stated differently, at lower temperatures, gas compresses according to the equation PV=nRT, therefore more gas can be contained in a chamber having a lower pressure.

Generally stated, the gas "packing effect" can be described by the ratio of room temperature to the coolant temperature. For liquid nitrogen, the packing effect can be expressed as 295/77 or 3.8. Thus, the packing effect for dry ice is about 295/195 or 1.51, while the value for the freezing point of water is only about 295/273 or 1.08. Thus, it is preferred that the coolant temperature be selected to provide a packing effect which is at least about 1.08, more preferably at least about 1.51 and most preferably at least about 3.8, although other values can be used. Of course, as noted above, preparing the container such as by evacuating and purging (to clean it before use) is important.

In one preferred embodiment, hyperpolarized $^3$He is collected in the cooled container or chamber. In another preferred embodiment, either $^3$He or $^{129}$Xe exits the polarizer cell 22 and is directed into a closed container 50A such that the hyperpolarized gas mixture (with the alkali metals removed) which exits the polarizer cell (e.g., the "exhaust" mixture) is captured and enclosed by the container. The container can then be sealed and allowed to warm to ambient temperature. This is unlike the cryogenic cold finger apparatus used to continuously process $^{129}$Xe (by retaining only the $^{129}$Xe and directing the remainder of the gas mixture out of the container). In addition, tubing and other chambers positioned after the polarizer cell 22 or transferor vessel can also be cooled.

In another aspect of a preferred embodiment, the cryo-cooled gas extraction is carried out under temperature control to provide a more "controlled" or exact filling amount of gas to be directed into the container. One way to control temperature during the cryo-cooling process is to direct cold nitrogen gas to flow across a heater element positioned proximate to the transport container. A temperature sensor can be positioned adjacent the transport container to measure temperature of the container. This information feeds back to the heater element to automatically turn it "off" or "on" so as to maintain the desired temperature of the transport vessel (between room temperature and the coolant temperature). This would allow variable temperature (from about 77 K to room temperature) across the transport container. This controlled temperature gradient can allow consecutive transfer or receiving vessels to be filled with (substantially) the same amount of hyperpolarized gas. This controlled amount is desired (within certain tolerance ranges) so that a precise dosage can be delivered or administered to a patient. For example, upon extraction of gas into a first container, the polarizer cell starts with a pressure of about 8 atm. However, before the next consecutive container is filled, the cell pressure could be depleted. Thus, one could control the rate of extraction via temperature gradients to control the amount of gas which exits the cell into the temperature controlled (temperature gradient) container to deliver a substantially equal amount to the two consecutively filled containers. Alternatively, multiple containers (not shown) can be plumbed to be filled simultaneously such as by concurrently engaging two or three or more (preferably similarly sized) containers with the polarization cell such that each is cooled to the same temperature. The hyperpolarized gas flow could be directed down an main exit channel and split into channels equidistant from the cell. Preferably the multiple containers have the same size, volume, and (cooled) temperature. The split channels direct the gas into the containers in communication therewith to obtain substantially the same amount of gas in each container.

G. Container/Materials

Because the shape of the container area can impact the rate of depolarization, it is preferred that container configurations be selected to maximize the free-gas volume of the container (V) while minimizing the surface area (A) which contacts the hyperpolarized gas (that is, to decrease the value of the ratio A/V). More preferably, the container is sized and configured to provide a A/V ratio of about less than 1.0, and even more preferably less than about 0.75. In one embodiment, the container is substantially spherical.

Preferred container materials include non-magnetic high-purity metal films, high-purity metal oxides, high purity insulators or semi-conductors (such as high purity silicon) and polymers. As used herein, "high purity" includes materials which have less than about 1 ppm ferrous or paramagnetic impurities and more preferably less than about 1 ppb ferrous or paramagnetic impurities. Preferred polymers for use in the containers described herein include materials which have a reduced solubility for the hyperpolarized gas. For the purposes of the inventions herein, the term "polymer" to be broadly construed to include homopolymers, copolymers, terpolymers and the like. Similarly, the terms "blends and mixtures thereof" include both immiscible and miscible blends and mixtures. Examples of suitable materials include, but are not limited to, polyolefins (e.g., polyethylenes, polypropylenes), polystyrenes, polymethacrylates, polyvinyls, polydienes, polyesters, polycarbonates, polyamides, polyimides, polynitriles, cellulose, cellulose derivatives and blends and mixtures thereof. It is more preferred that the coating or surface of the container comprise a high-density polyethylene, polypropylene of about 50% crystallinity, polyvinylchloride, polyvinylflouride, polyamide, polyimide, or cellulose and blends and mixtures thereof.

Of course, the polymers can be modified. For example, using halogen as a substituent or putting the polymer in deuterated (or partially deuterated) form (replacement of hydrogen protons with deuterons) can reduce the relaxation rate. Methods of deuterating polymers are known in the art. For example, the deuteration of hydrocarbon polymers is described in U.S. Pat. Nos. 3,657,363, 3,966,781, and 4,914,160, the disclosures of which are hereby incorporated by reference herein. Typically, these methods use catalytic substitution of deuterons for protons. Preferred deuterated hydrocarbon polymers and copolymers include deuterated paraffins, polyolefins, and the like. Such polymers and copolymers and the like may also be cross-linked according to known methods.

It is further preferred that the polymer be substantially free of paramagnetic contaminants or impurities such as color centers, free electrons, colorants, other degrading fillers and the like. Any plasticizers or fillers used should be chosen to minimize magnetic impurities contacting or positioned proximate to the hyperpolarized noble gas.

Alternately, in another embodiment, the contact surface can be formed from a high purity metal. The high purity metal can provide advantageously low relaxivity/depolarization resistant surfaces relative to hyperpolarized noble gases.

As noted above, any of these materials can be provided as a surface coating on an underlying substrate or formed as a material layer to define a friendly contact surface. If used as a coating, the coating can be applied by any number of techniques as will be appreciated by those of skill in the art (e.g., by solution coating, chemical vapor deposition, fusion bonding, powder sintering and the like). Hydrocarbon grease can also be used as a coating. The storage vessel or container can be rigid or resilient. Rigid containers can be formed of Pyrex™ glass, aluminum, plastic, PVC or the like. Resilient vessels are preferably formed as collapsible bags, preferably collapsible polymer or metal film bags. Examples of materials which can provide oxygen resistance as well as low-solubility include but are not limited to PET (polyethylene terphthalate), PVDC (polyvinylidene dichloride), Tedlar™ (polyvinylfluoride), cellophane and polyacrylonitrile.

Preferably, care is taken to insure all fittings, seals, and the like which contact the hyperpolarized gas or which are located relatively near thereto are manufactured from materials which are friendly to polarization or which do not substantially degrade the polarized state of the hyperpolarized gas. For example, many commercially available seals are made from fluoropolymers which (with the exception of Tedlar™ noted above) are not particularly good for the preservation of either $^{129}$Xe or $^3$He hyperpolarized gases because of the solubility of the hyperpolarized gas in the material.

Inasmuch as most common gasket materials are fluoropolymers, they can potentially have a substantially depolarizing effect on the gas. This effect, which can be particularly acute for $^3$He, can be attributed to a relatively high solubility of helium in most fluoropolymers due to the larger void space in the polymer attributable to the large fluorine atoms. It is preferred that the containers of the present invention employ seals, O-rings, gaskets and the like with substantially pure (substantially without magnetic impurities) hydrocarbon materials such as those containing polyolefins (including but not limited to polyethylene, polypropylene, copolymers and blends thereof). Additionally, hydrocarbon grease can be used to further facilitate or produce a vacuum tight seal. Thus, if a valve is used to contain the gas in the chamber 30, it is preferably configured with a magnetically pure (at least the surface) O-ring and/or with hydrocarbon grease. Of course, where fillers and plasticizers are employed, then it is preferred that they be selected to minimize the magnetic impurities such as substantially pure carbon black.

In an alternative embodiment, the O-ring seal can be configured with the exposed surface coated with a high purity metal as discussed for the container surface.

Similarly, the O-ring or seal can be coated or formed from an outer exposed layer of a polymer at least "$L_p$" thick. the inner layer thickness ("$L_{th}$") is at least as thick as the polarization decay length scale ("$L_p$") which can be determined by the equation:

$$L_p = \sqrt{T_p D_p}$$

where $T_p$ is the noble gas nuclear spin relaxation time in the polymer and $D_p$ is the noble gas diffusion coefficient in the polymer.

For example, a layer of substantially pure polyethylene can be positioned over a commercially available O-ring. One preferred O-ring material for $^{129}$Xe is a Teflon™ coated rubber.

When bags with long surface relaxation times are used, other relaxation mechanisms can become important. One of the most important additional relaxation mechanisms is due to collisions of the noble gas with paramagnetic oxygen. Because $O_2$ has a magnetic moment, it can relax hyperpolarized gases in the same manner as protons. Given this problem, care should be taken to reduce the oxygen content in the storage container through careful preconditioning of the container, such as by repeated evacuation and pure gas purging procedures. Preferably, the container is processed such that the $O_2$ concentration yields a $T_1$ of about 1000 hours or more. More preferably, the container is processed to obtain an $O_2$ concentration on the order of about $6.3 \times 10^{-6}$ atm or less or about $10^{-7}$ atm or less, and even more preferably less than about $1 \times 10^{-10}$ atm. Additionally, as discussed above, the evacuation/purge procedures can include heating the container or other evacuating or pumping methods to additionally facilitate the removal of any remaining (monolayer) residual amounts of moisture or water.

Preferably, the patient interface and storage chambers and associated apparatus and tubing are prepared in advance of use to minimize any preparation required at the hospital or extraction site. Therefore, preferred pre-conditioning or equipment preparation methods such as cleaning, evacuating, and purging the connectable tubing and patient delivery vessel (see FIG. 3, 250, 251) or other components to remove oxygen and paramagnetic contaminants are preferably done off-site. After preparation/conditioning, the tubing 251 and delivery bag 250 can be stored at the hospital for use under pressure with a noble gas or benign liquid therein. This pre-filled gas or fluid storage can minimize the potential for the containers or components to de-gas (gas from the matrix of a material such as oxygen can migrate into the chamber onto the contact surfaces), and can also minimize air leaking into the container. Alternatively, or in addition to the pre-conditioning, the pressurized tubing and delivery vessels (and/or syringes) can be sealed with check valves or other valved ports. In another alternative, vacuum tight valves can allow the tubes and containers to be stored for use under vacuum rather than under positive pressure.

H. Calibration Station

Preferably, prior to introduction and/or delivery to a patient, the hyperpolarized gas is preferably calibrated for identification of the efficacy or polarization strength of the gas. Advantageously, this calibration will allow a "shelf-life" to be affixed to the delivery container alerting personnel as to the temporally limited useful life of the product. This positive identification can minimize the delivery of non-effective hyperpolarized gas to the patient. In a preferred embodiment, the calibration is performed on the hyperpolarized gas at the end use site. Preferably, the calibration is performed on the gas subsequent to when it has been extracted from the shipping or transport container 50A–E. More preferably, the hyperpolarized gas is calibrated when the gas is captured in the delivery vessel 250. It is also preferred that the gas be calibrated when it is positioned in a protected area (i.e., stable magnetic field) proximate to the end use site at the clinic or hospital facility. This allows a reliable representative calibration to be established on the product when it is in its final delivery container, or at its destination site, and/or when it is in a protected environment (such as proper shielding and/or homogenous magnetic fields) and is protected from potentially degrading elements (i.e., EMI, etc.) especially problematic during shipping. Also preferably, after calibration the container is configured with an external indicia of validation/inspection corresponding to an inspection date and a use-by date and or time.

In a preferred embodiment, the transport container is sized and configured to ship multiple dosages of the hyperpolarized gas, and then extracted at a protected destination site to form single dose patient delivery vessels. The single dose vessels can be tested for efficacy and externally dated/ stamped or otherwise encoded with a preferred use date/ time. This calibrated and externally visually identified product will allow operators to conveniently identify and remove "old" or "depolarized" product in advance of the patient delivery/end use.

Figure 15:
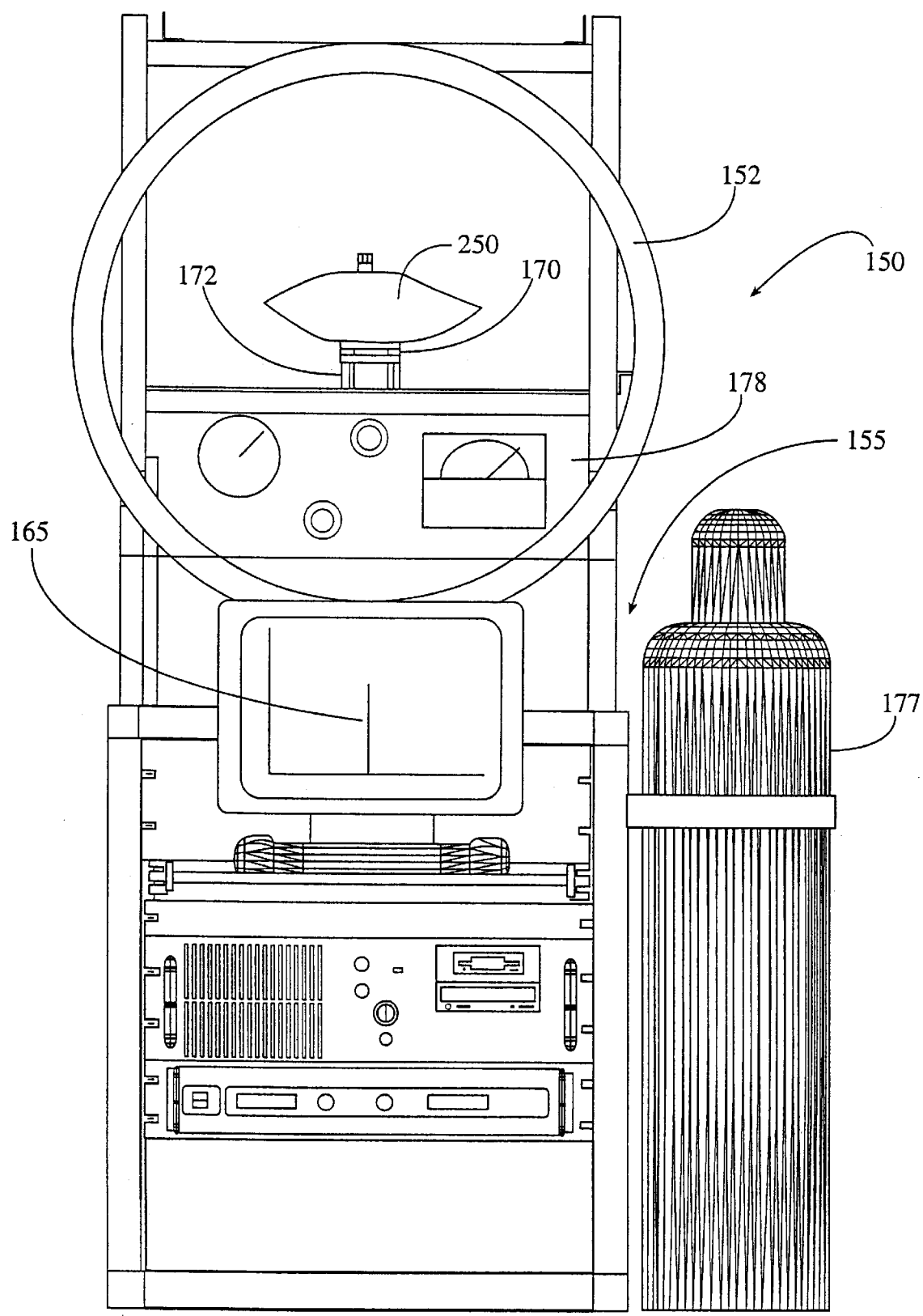
FIG. 15 is a schematic representation of a polarization determination or calibration station according to the present invention.

Generally described, as shown in FIG. 15, the calibration is carried out at a calibration station 150 which preferably uses a low-field NMR spectrometer 155 to transmit RF pulses to surface coils 160 positioned proximate to the hyperpolarized gas sample. The spectrometer then receives at least one signal 165 back corresponding to the hyperpolarized gas which are processed to determine the polarization level of the hyperpolarized gas (preferably contained in a single dose patient delivery vessel). As shown, the calibration station 150 preferably includes a set of Helmholtz coils 152 (preferably of about 24 inches in diameter) to provide the low magnetic field and a (NMR) surface coil 170 (preferably sized and configured at about 1 inch in diameter and with about 350 turns). The surface coil 170 sits on a platform 172 to preferably position the surface coil 170 in the center of the Helmholtz coils 152. The term "low field" as used herein includes a magnetic field under about 100 Gauss. Preferably, the calibration station is configured with a field strength of about 5–40 gauss, and more preferably a field strength of about 20 gauss. Accordingly, the corresponding $^3$He signal frequency range is about 16 kHz–128 Khz, with a preferred frequency of about 64 kHz. Similarly, the $^{129}$Xe signal frequency range is about 5.9 kHz–47 kHz, with a preferred signal frequency of about 23.6 kHz.

Preferably, the container 250 is positioned on the top surface of the surface coil 170 and substantially in the center of the Helmholtz coils 152. Generally described, in operation, a selected RF pulse (of predetermined pulse, frequency, amplitude, and duration) is transmitted from the NMR device 155 to the surface coil 170. The frequency corresponds to the field strength of the magnetic field and the particular gas, examples of which are noted above. This RF pulse generates an oscillating magnetic field which misaligns at least some of the hyperpolarized $^3$He or $^{129}$Xe nuclei from their static magnetic field alignment position. The misaligned nuclei start processing at their associated Larmour frequency (corresponding to pulse frequency). The precessing spins induce a voltage in the surface coil which can be processed to represent a signal 165. The voltage is received back (typically amplified) at the computer and the signal fits an exponentially decaying sinusoid pattern. As shown, the signal 165 received back at the computer is the Fourier transform of the received signal. The peak-to-peak voltage of this signal is directly proportional to polarization (using a known calibration constant). The computer can then calculate the polarization level, and generate calculated preferred use dates and times associated with desired polarization levels. As will be recognized by those of skill in the art, other calibration or hyperpolarization level determination methods can also be employed and still be within the product identification and calibration or product-use or expiration determination methods contemplated by the present invention. For example, detecting the minute magnetic field generated by the polarized $^3$He spins. Also, as shown in FIG. 15, a purge gas cylinder 177 and associated vacuum and purge equipment 178 are positioned proximate to the calibration station. In one preferred embodiment, the purge and vacuum equipment are positioned on or proximate to the calibration station so that the container can be cleaned (evacuated and pure-gas purged) at the calibration station 150 prior to the calibration. Thus, the calibration station can advantageously be combined with a filling and cleaning station. For example, a rigid transport vessel can transport the hyperpolarized gas from a hyperpolarization site to the calibration station at a use site. The delivery container 250 can be cleaned at the calibration station (or pre-cleaned as discussed above). The gas can be extracted from the transport container into the delivery container 250 right at the calibration station, preferably according to one of the methods of the instant invention. The extracted gas now captured in the container 250 can be easily and instantly measured or identified/calibrated as to its efficacy or hyperpolarization level and marked for instant or future use.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means plus function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be within the scope of the appended claims. The invention is defined by the following claims with equivalents of the claims to be included therein.

That which is claimed:

1. A method of removing hyperpolarized gas from a vessel, comprising the steps of:

positioning a resilient member in fluid communication wit the internal chamber of a container holding hyperpolarized gas, wherein the resilient member includes at least one surface which is coated with or formed from a material which inhibits depolarization of the hyperpolarized gas;

expanding the resilient member to extend into the container to contact the hyperpolarized gas; and forcing the hyperpolarized gas to exit the container away from the expanded resilient member.

2. A method according to claim 1, wherein the container includes an inlet port and exit port positioned on opposing sides of the container, and wherein the resilient member is securely attached to the inlet port such that fluid introduced therein acts to inflate the resilient member and the hyperpolarized gas exits the container through the exit port.

3. A method according to claim 1, wherein the method further comprises the step of deflating the resilient member.

4. A method according to claim 1, wherein the resilient member has a collapsed configuration and at least one expanded configuration, wherein the container includes a first port and a spaced apart second port and the resilient member is disposed in the container to be expandable in a desired direction between the first and second ports, and wherein the expanding step comprises inflating the resilient member to extend so in a direction that positions the leading edge portion thereof to reside closer to one of the first and second ports compared to its collapsed configuration.

5. A method according to claim 1, wherein the hyperpolarized gas comprises $^3$He.

6. A method according to claim 1, wherein the hyperpolarized gas comprises $^{129}$Xe.

7. A method according to claim 1, wherein the resilient member is sealably attached to the container in a leak-resistant manner.

8. A method according to claim 1, wherein the expanding step is carried out by introducing a fluid into the container on a first primary side of the resilient member and expelling the hyperpolarized gas on the opposing primary side of the resilient member.

9. A method according to claim 8, wherein the fluid comprises nitrogen gas.

10. A method of removing hyperpolarized gas from a vessel, comprising the steps of:

positioning a resilient member in fluid communication with the internal chamber of a container holding hyperpolarized gas;

expanding the resilient member to extend into the container to contact the hyperpolarized gas; and forcing the hyperpolarized gas to exit the container away from the expanded resilient member, wherein the expanding step is carried out by introducing a fluid into the container on a first primary side of the resilient member and expelling the hyperpolarized gas on the opposing primary side of the resilient member and wherein the fluid comprises nitrogen, and wherein to nitrogen is allowed to cross the resilient member to mix with the hyperpolarized gas during the forcing step.

11. A method according to claim 8, wherein the fluid comprises nitrogen, and wherein the nitrogen is substantially captured on the first side of the resilient member and inhibited from mixing with the hyperpolarized gas during the forcing step.

12. A vessel for holding a quantity of hyperpolarized noble gas, comprising:

a chamber;

a quantity of hyperpolarized noble gas disposed in said chamber; and a resilient member in communication with said hyperpolarized gas in said chamber, said resilient member having a first collapsed position and a second expanded position, wherein when in said second position said resilient member extends into said chamber a thither distance than when in said first position, wherein the resilient member includes at least one primary surface which is coated with or formed from a material which inhibits depolarization of the hyperpolarized gas.

13. A vessel according to claim 12, wherein said vessel further comprises a fluid inlet port and an exit port in fluid communication with said chamber.

14. A vessel according to claim 13, wherein said resilient member translates to said second position responsive to fluid introduced into said inlet port.

15. A vessel according to claim 14, wherein said resilient member is sealed to a portion of said chamber such that said resilient member is positioned intermediate of said inlet port and said hyperpolarized gas and wherein said resilient member inhibits said hyperpolarized gas from contacting said fluid inlet port.

16. A vessel according to claim 12, wherein said hyperpolarized gas comprises $^3$He.

17. A vessel according to claim 12, wherein said hyperpolarized gas comprises $^{129}$Xe.

18. A vessel according to claim 12, wherein said vessel further comprises at least one valve in communication with said exit port to controllably release the hyperpolarized gas therefrom.

19. A vessel according to claim 12, wherein said resilient member has opposing first and second primary surfaces, and wherein said vessel further comprises an extraction fluid held on the side of the first primary surface and the hyperpolarized gas is held on the side of the second primary surface, and wherein said resilient member is sealed to the vessel in a manner that inhibits the extraction fluid from contacting the hyperpolarized gas.

20. A vessel according to claim 12, wherein said resilient member has opposing first and second primary surfaces, and wherein said vessel further comprises an extraction fluid held on the side of the first primary surface and the hyperpolarized gas is held on the side of the second primary surface, and wherein said resilient member is attached to the vessel in a manner that allows the extraction fluid to contact the hyperpolarized gas.

* * * * *

UNITED STATES PATENT AND TRADEMARK OFFICE
CERTIFICATE OF CORRECTION

PATENT NO.    : 6,543,236 B2
DATED         : April 8, 2003
INVENTOR(S)   : Zollinger et al.

It is certified that error appears in the above-identified patent and that said Letters Patent is hereby corrected as shown below:

Column 22,
Line 39, should read as follows:
-- positioning a resilient member in fluid communication with --

Signed and Sealed this

Fifteenth Day of July, 2003

JAMES E. ROGAN
*Director of the United States Patent and Trademark Office*